US009079765B2

(12) United States Patent
Himmler et al.

(10) Patent No.: US 9,079,765 B2
(45) Date of Patent: Jul. 14, 2015

(54) NANOPARTICLES COMPRISING ANTIGENS AND ADJUVANTS, AND IMMUNOGENIC STRUCTURES

(75) Inventors: Gottfried Himmler, Vienna (AT); G. C. Mudde, Breitenfurt (AT); Ralf Kircheis, Vienna (AT); Thomas William Rademacher, Oxford (GB); Soledad Penades Ullate, San Sebastian (ES); Manuel Martin Lomas, San Sebastian (ES); Jose Luis De Paz Carrera, Seville (ES); Rafael Ojeda Martinez De Castilla, Seville (ES); Africa Garcia Barrientes, Madrid (ES)

(73) Assignee: Midatech Ltd., Abingdon, Oxford, Oxfordshire (GB)

( * ) Notice: Subject to any disclaimer, the term of this patent is extended or adjusted under 35 U.S.C. 154(b) by 1860 days.

(21) Appl. No.: 11/576,415

(22) PCT Filed: Sep. 30, 2005

(86) PCT No.: PCT/GB2005/003791
§ 371 (c)(1),
(2), (4) Date: Sep. 24, 2007

(87) PCT Pub. No.: WO2006/037979
PCT Pub. Date: Apr. 13, 2006

(65) Prior Publication Data
US 2009/0104268 A1   Apr. 23, 2009

Related U.S. Application Data

(60) Provisional application No. 60/692,232, filed on Jun. 21, 2005, provisional application No. 60/615,182, filed on Oct. 1, 2004.

(51) Int. Cl.
| A61K 9/14 | (2006.01) |
| A61K 39/00 | (2006.01) |
| A61P 37/00 | (2006.01) |
| B82Y 5/00 | (2011.01) |
| A61K 39/39 | (2006.01) |
| A61K 47/48 | (2006.01) |

(52) U.S. Cl.
CPC ............... *B82Y 5/00* (2013.01); *A61K 39/0011* (2013.01); *A61K 39/39* (2013.01); *A61K 47/4833* (2013.01); *A61K 47/48861* (2013.01); *A61K 47/48884* (2013.01); *A61K 2039/55555* (2013.01); *A61K 2039/6037* (2013.01); *A61K 2039/625* (2013.01); *A61K 2039/645* (2013.01)

(58) Field of Classification Search
None
See application file for complete search history.

(56) References Cited

U.S. PATENT DOCUMENTS

| 7,186,398 | B2 * | 3/2007 | Andres et al. ............... 424/9.1 |
| 7,192,778 | B2 * | 3/2007 | Natan ............................. 436/56 |
| 7,332,586 | B2 * | 2/2008 | Franzen et al. ............... 530/402 |
| 7,344,887 | B2 * | 3/2008 | Salem et al. .................. 435/459 |
| 7,998,923 | B2 * | 8/2011 | Pinaud et al. ................. 514/1.1 |
| 2007/0014804 | A1 * | 1/2007 | Burkhard ..................... 424/184.1 |

FOREIGN PATENT DOCUMENTS

| EP | 0429816 | 6/1991 |
| WO | 98/43677 | 10/1998 |
| WO | 02/32404 | 4/2002 |

OTHER PUBLICATIONS

Doolan and Hoffman (2000) "The Complexity of Protective Immunity Against Liver-Stage Malaria", The Journal of Immunology, 165: 1453-62.*
Wang, et al. (2004) "Binding of High-Mannose-Type Oligosaccharides and Synthetic Oligomannose Clusters to Human Antibody 2G12: Implications for HIV-1 Vaccine Design", Chemistry & Biology, 11(1): 127-34.*
Linzer, et al. (Nov. 1985) "Structural Studies of the Rhamnose-Glucose Polysaccharide Antigen from *Streptococcus sobrinus* B13 and 6715-T2", Infection and Immunity, 50(2): 583-85.*
http://www.who.int/mediacentre/factsheets/fs094/en/, "Malaria", author unknown, no journal, downloaded Dec. 20, 2014, Published by the World Health Organization, 8 pages long.*
http://hivinsite.ucsf.edu/hiv?page=basics-00-13, author unknown, no journal/volume/issue no., published 2011 by the Regents of the University of California online, San Francisco, CA, downloaded Dec. 21, 2014, 1 page long.*
http://www.cdc.gov/vaccines/vpd-vac/vpd-list.htm, downloaded Dec. 21, 2014, published by the Centers for Disease Control and Prevention, USA, Atlanta, GA, No journal/volume/issue, 2 pages long.*
http://doctors-hospitals-medical-cape-town-south-africa.blaauwberg.net/human_diseases_and_disorders/list_of_viral_diseases, downloaded Dec. 21, 2014, no journal/volume/issue, author unknown, published by Blaauwberg Online, 3 pages long.*
A. Barrientos et al., "Gold Glyconanoparticles: Synthetic Polyvalent Ligands Mimicking Glycocalyx-Like Surfaces as Tools for Glycobiological Studies", Chem. Euro. J., 9: 1909-1921 (2003).
J. Rojo et al., "Gold Glyconanoparticles as New Tools in Antiadhesive Therapy", ChemBioChem, 5: 291-297 (2004).
J. De La Fuente et al., "Understanding carbohydrate-carbohydrate interactions by means of glyconanotechnology", Glycoconjugate Journal, 21: 149-163 (2004).

(Continued)

*Primary Examiner* — Robert M Kelly
(74) *Attorney, Agent, or Firm* — Patrick J. Hagan; Dann, Dorfman, Herrell and Skillman, P.C.

(57) ABSTRACT

Nanoparticles comprising adjuvants and antigens, such as tumor and pathogen antigens, are disclosed and their use in a range of applications such as for the treatment of cancer and infectious diseases. Immunogenic structures based on nanoparticles or antibodies with carbohydrate ligands, and their use for therapeutic and prophylactic purposes, and for the isolation and detection of antibodies directed against the carbohydrate structures.

26 Claims, 11 Drawing Sheets

(56) References Cited

OTHER PUBLICATIONS

R. Lo-Man et al., "A Fully Synthetic Therapeutic Vaccine Candidate Targeting Carcinoma-Associated Tn Carbohydrate Antigen Induces Tumor-Specific Antibodies in Nonhuman Primates", Cancer Research, 64: 4987-4994 (2004).

M. Zheng et al., J. Am. Chem. Soc., "Nanoparticles Comprising a Mixed Monolayer for Specific Bindings with Biomolecules", 126: 12047-12054 (2004).

T. Fifis et al., "Size-Dependent Immunogenicity: Therapeutic and Protective Properties of Nano-Vaccines against Tumors", Journal of Immunology, 173: 3148-3154 (2004).

P. Livingston et al., "Carbohydrate vaccines that induce antibodies against cancer. 2. Previous experience and future plans", Cancer Immunol. Immunother., 45: 10-19 (1997).

M. Reddish et al., "Specificities of anti-sialyl-Tn and anti-Tn monoclonal antibodies generated using novel clustered synthetic glycopeptide epitopes", Glycoconjugate Journal, 14: 549-560 (1997).

G. Ada et al., "Carbohydrate-protein conjugate vaccines", Clinical Microbiology and Infection, 9: 79-85 (2003).

G. Ada., "Vaccines and Vaccinations", 345: 1042-1053 (2001).

* cited by examiner

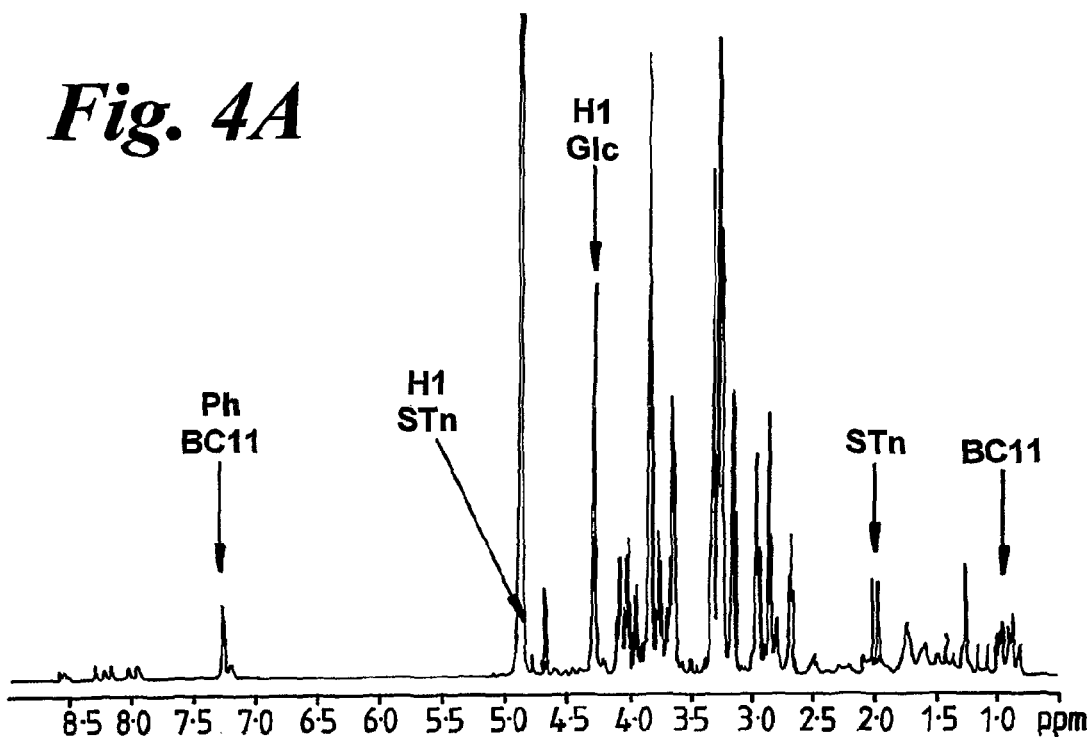
*Fig. 4A*
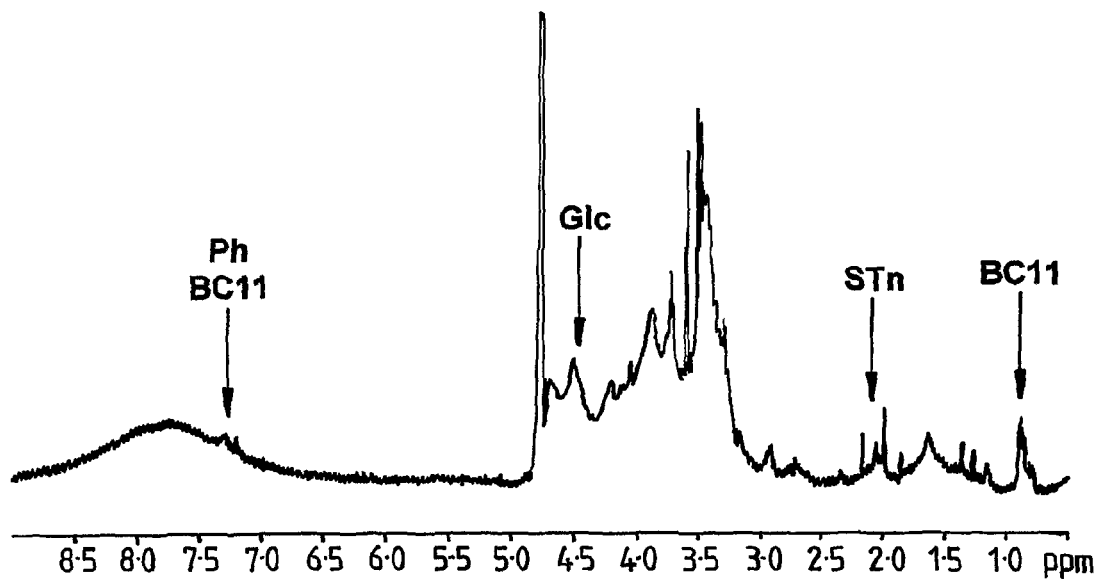

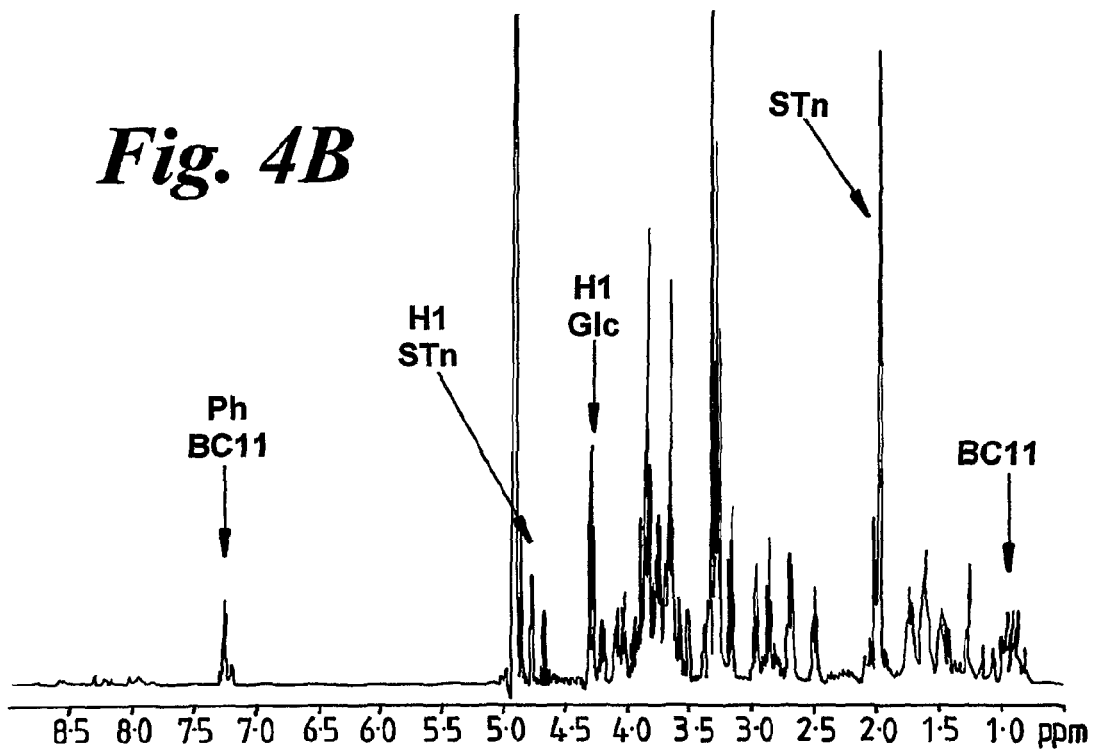
*Fig. 4B*
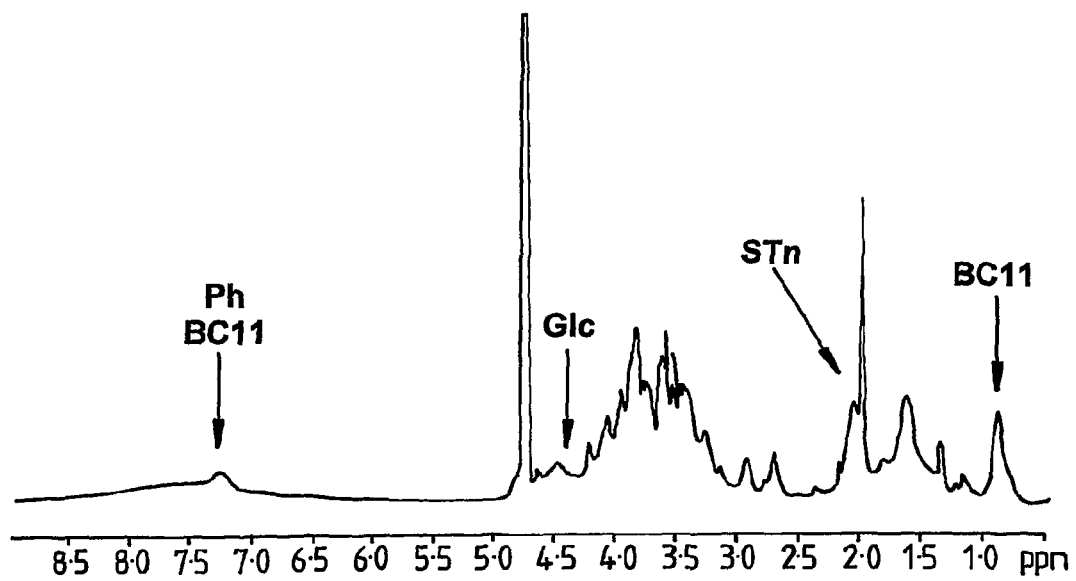

NANOPARTICLES COMPRISING ANTIGENS AND ADJUVANTS, AND IMMUNOGENIC STRUCTURES

CROSS-REFERENCE TO RELATED APPLICATIONS

This application is the U.S. National Stage of International Application No. PCT/GB2005/003791, filed Sep. 30, 2005, which claims priority from U.S. Provisional Application No. 60/615,182, filed Oct. 1, 2004 and U.S. Provisional Application No. 60/692,232, filed Jun. 21, 2005. The disclosures of the aforesaid applications are incorporated by reference in their entireties in the present application.

FIELD OF THE INVENTION

The present invention relates to nanoparticles, and more particularly to nanoparticles comprising adjuvants and antigens, such as tumour and pathogen antigens, and their use in a range of applications. The present invention further relates to immunogenic structures with carbohydrate ligands, and their use for therapeutic and prophylactic purposes, and for the isolation and detection of antibodies directed against the carbohydrate structures.

BACKGROUND OF THE INVENTION

The use of carbohydrate and peptide antigens in vaccines is greatly hampered by their lack of immunogenicity when injected directly into a patient. Such antigens, when injected alone, are usually ignored by antigen-presenting cells (APCs), cleared rapidly and do not induce an immune response.

In most cases, it is also necessary to administer the antigen in combination with an adjuvant. The adjuvant may be a simple delivery system such as liposomes, which slow clearance of the antigen and make it more likely to reach and be taken up by APCs. However, this in itself is not very effective and usually needs to be combined with agents that stimulate the immune system, such as bacterial products which stimulate cytokine formation. Cytokines themselves may also be co-administered. Many of these products are too toxic or too experimental to be used in humans, and the most effective adjuvants are not approved for human use. Most of the adjuvants available for use in humans are of limited effectiveness. Finding effective adjuvants suitable for human use is a continuing challenge.

Carbohydrate antigens are of particularly weak immunogenicity because they can stimulate only B-cell and not T-cell responses. This is usually addressed by conjugating the carbohydrate to a protein carrier. However, in order to raise an immune response it is also necessary to use an adjuvant.

Carbohydrate antigens are potential targets for anti-cancer immunotherapy since they are exposed at the surface of tumour cells but hidden on normal cells. Many bacteria and other pathogens are also distinguished by carbohydrate antigens which would be a good target for vaccines, if carbohydrates were not so poorly immunogenic. Improving the immunogenicity of carbohydrate antigens would thus have applications in a wide variety of therapeutic fields.

Cancer cells almost always are glycosylated in an aberrant manner, a characteristic that distinguishes them from normal cells. (Glycoconjugate J. (1997), 14:569; Adv. Cancer Res. (1989), 52:257; Cancer Res. (1996), 56:5309). In most cases, the aberrant glycosylation is presented on the surface of the cells in the form of glycoproteins and glycolipids. These altered carbohydrate structures can therefore be called tumour associated antigens (TAA), which often do not occur on normal cells. In many cases, cells do not show a homogeneous glycosylation, i.e. different glycoforms of complex glycan-chains exist on one cell surface (Annu. Rev. Biochem. (1988), 57:785).

In the course of the discovery and the subsequent characterisation of the most varied tumour associated antigens, research has shown that they have important functions for the cancer cells. For example, the tumour associated antigens enable the degenerate cells to show properties characteristic of the malignant phenotype, such as an increased capability for adhesion, which play an important role in establishing metastases. However, such antigens can at certain stages also be expressed on normal cells where they are responsible for the normal functions of these cells. Thus, tumour associated antigens are structures which are predominantly presented by tumour cells, generally on or in the cell membrane, and which allow them to be differentiated from non-malignant tissue. Tumour associated antigens may be, for example, polypeptides, in particular glycosylated proteins, or glycosylation patterns of polypeptides. Other structures which may represent a tumour associated antigen include glycolipids, for example, gangliosides, such as GM2. Such tumour associated antigens may be represented by changes in the composition of lipids of the cell membrane which may be characteristic of cancer cells. Tumour associated antigens include the following examples.

N-CAM (Neuronal Cell Adhesion Molecule), which is often expressed on tumours of neuronal origin and which effects homophilic adhesion (J. Cell Biol. 118 (1992), 937).

The Lewis Y carbohydrate antigen, which occurs on the majority of tumours of epithelial origin, but which also plays an important role during the fetal development of epithelial tissues. It has been shown that the expression of this antigen in lung cancer is strongly associated with an unfavourable prognosis since Lewis Y positive cancer cells obviously have a higher metastatic potential (N. Engl. J. Med. 327 (1992), 14).

CEA (Carcino Embryonic Antigen), which often occurs on epithelial tumours of the gastrointestinal tract and which has been identified as a self-adhesion molecule (Cell 57 (1989), 327).

Ep-CAM (Epithelial Cell Adhesion Molecule), which is expressed on nearly all tumours of epithelial origin, but which also occurs on a large number of normal epithelia. It has been characterized as a self-adhesion molecule and can therefore be classified as a pan-epithelial adhesion antigen (J. Cell Biol. 125 (1994), 437).

Further examples of tumour-associated antigens are Sialyl Tn carbohydrate, Lewis antigens (Lewis-x, Lewis-b, Lewis y-structures), Globo H carbohydrate, gangliosides such as GD2/GD3/GM2, Prostate Specific Antigen (PSA), CA 125, CA 19-9, CA 15-3, TAG-72, EGF receptor, Her2/Neu receptor, p97, CD20 and CD21. Monoclonal antibodies directed against all these antigens are available. Examples of tumour associated antigens are described in DeVita et al. (Eds., "Biological Therapy of Cancer", 2. Edition, Chapter 3: Biology of Tumor Antigens, Lippincott Company, ISBN 0-397-51416-6 (1995), (Elektrophoresis (1999), 20:362; Curr. Pharmaceutical Design (2000), 6:485, Neoplasma (1996), 43:285)).

There are various methods of treatment of cancer, yet the success rate of the present treatments regimens is still to be improved. Aside from surgery and chemotherapy, immunotherapeutic treatment is also known.

In passive immunotherapy, monoclonal antibodies (MAbs) are administered systemically to a patient in a suitable amount to directly bind to a target. The aim of the treatment is to form an immune complex and through a series of immune reactions the cell or organism afflicted with the target is killed. The therapeutic effect is depending on the concentration of the MAbs in the circulation and their biological half-life, which is usually quite short. It is therefore necessary to repeat the administration within an appropriate timeframe. If xenogeneic MAbs, such as murine antibodies, are used adverse reactions are expected, possibly leading to anaphylactic shock. Because of this drawback, such immunotherapies are employed for a limited time only.

Active immunization regimens activate the immune system of patients in a different way. Following the administration of an antigen that resembles a specific target, the patient's humoral and T-cell specific immune response induces defence mechanisms to combat the target in vivo. Vaccine antigens of various types and against a wide variety of different diseases are well known in the art. For example, vaccination against Hepatitis B using vaccines containing surface hepatitis B antigens are well known. It has been shown that high dose ranges of antigens used for vaccination of as well as low dose vaccination can give sufficient rates of seroconversion (Parish D. C. et al., 1991, Southern Medical Journal, 84, 426-430; Goudeau A. et al., 1984, The Lancet, 10, 1091-1092).

Mannan-mucin fusion proteins are also known and can be used for generating cytotoxic T cells. It has been shown that depending on the dosage of the administered fusion protein to mice, either almost only cellular immunity (low doses) or only humoral immunity (high doses) can be induced (Pietersz G. A. et al., 1998, Cancer Immunol. Immunother., 45, 321-326).

For active immunization, the antigens are usually presented in an immunogenic formulation to provide a vaccine. Antigens mimicking the targets have either similarities in the primary and secondary sequence of the targets or fragments thereof. Mimotopes or mimotopic antigens, however, have similarities in the tertiary structure of the target.

Although many products have been developed for the treatment of cancer there is still a high demand on providing substances which have improved characteristics compared to the already known substances. In particular, in the field of vaccination, there is a need in products that are highly immunogenic, easily reproducible and highly effective, but do not cause severe side effects.

WO 02/32404 (Consejo Superior de Investigaciones Scientificas) discloses nanoparticles formed from metal or semiconductor atoms in which ligands comprising carbohydrates are covalently linked to the core of the nanoparticles. These nanoparticles are used for modulating carbohydrate mediated interactions and are soluble and non-toxic. PCT application claiming priority from GB-A-0313259.4 (Consejo Superior de Investigaciones Scientificas and Midatech Limited) discloses magnetic nanoparticles having cores comprising passive and magnetic metal atoms, the core being covalently linked to ligands. GB application 0411537.4 (Consejo Superior de Investigaciones Scientificas and Midatech Limited) discloses nanoparticles including magnetic nanoparticles which are conjugated to RNA ligands, in particular siRNA ligands.

SUMMARY OF THE INVENTION

Broadly, the present invention relates to nanoparticles comprising adjuvants and antigens and immunogenic structures with carbohydrate ligands.

In one aspect, the present invention provides improved immunogenic structures which can be used for the treatment of various diseases, and in particular for vaccination purposes in the prophylaxis and treatment of cancer.

Accordingly, the present invention provides an immunogenic structure consisting of a core molecule covalently linked to a carbohydrate ligand and at least one T-cell helper peptide ligand.

In a further aspect, the present invention provides an immunogenic structure consisting of a core molecule covalently linked to a plurality of carbohydrate ligands and wherein the carbohydrate ligands comprise at least one neoepitope structure.

The core molecules may be antibodies or derivatives or fragments thereof. Alternatively the core molecules can also be nanoparticles consisting of a core of metal or semiconductor atoms, as described further herein. For example, the metallic core can comprise Au, Ag, Cu, Pd or Al. Nanoparticles and their production are described in detail in the WO 02/32404 and by Crespo et al, Physical Review Letters, 93(8): 87204-14, 2004.

An immunogenic structure according to the invention may be any carbohydrate ligand. For example, in preferred embodiments, it may show structural or functional similarity with carbohydrate-based tumour associated antigens, such as Lewis antigens, either sialylated or unsialylated, or Sialyl Tn or unsialylated Tn or indeed any of the tumour associated antigens discussed in the background section above.

The single carbohydrate ligand may also comprise a neoepitope structure. Neoepitopes may be formed by the glycosylation of an antigen of a cellular surface protein. Carbohydrate structures are rarely located on tumour cells as single molecules, but are mostly in clusters consisting of a plurality of carbohydrate structures. These clusters may form neoepitopes in which single ligands do not mediate antibody binding and destruction of the tumour cell, but instead an efficient immune response is a result of the recognition of the carbohydrate clusters. Carbohydrate clusters as occurring on tumour cells may be designed and mimicked by using a plurality of carbohydrate ligands, so that a huge amount of ligands in high densities are presented. These ligands can be tightly linked to the core molecule and imitate a cluster, i.e. a structure as presented on tumour cells.

By way of example, an antibody can bind to the aberrantly glycosylated structure on a tumour cell, but cannot bind to a single carbohydrate ligand presented on a surface structure. The inventive combination of carbohydrate ligands which are derived from these glycoproteins, optionally with further antigens of the aberrant glycosylation, therefore is possible and can result in the determination of neoepitope structures.

By the immunotherapy with the target of the aberrant glycosylation, practically all tumour-specific receptors which are characterized by this aberrant glycosylation can be blocked. Among them are, for example all the receptors of the EGF-receptor family, the CD55 (791Tgp72/DAF—decay accelerating factor) receptor, the transferrin receptor, and the P-glycoprotein.

It has also been found that immunogenic structures which are directed against aberrant glycosylation bind in a functional manner to several receptors of the family of the EGF receptors and thus the signal cascade for inducing the cell growth can effectively be blocked. Binding of growth factors to the receptors was thereby prevented or reduced, respectively. This treatment is more specific as compared to immunotherapy using antibodies against the proteinaceous extracellular part of the EGF receptor, since the unusual tumour-associated carbohydrate structures are missing on the EGF receptors of normal cells. On the other hand, the treatment is more universal, since simultaneously different receptors having the same aberrant glycosylation are blocked.

By the use of the immunotherapy, directed against an aberrant glycosylation, it is also possible to prevent or reduce the mitogenic stimulation of a cancer cell by EGF or heregulin. The specific binding of the antibodies to a tumour-associated glycosylation of cancer cells blocks the interaction of the receptors of growth factors with their physiologic ligands and inhibits the signal transduction through these receptors and thus the cell growth.

At the same time, such an antibody can specifically attack the tumour cell by its effect within the humoral and cellular immune system. Tumour cells which express the EGF receptor or receptors of the EGF receptor family, respectively, according to the invention, are specifically bound and can be lysed or blocked in growth.

Immunotherapy with the target of the neoepitope has been improved insofar as epithelial cells of normal tissue will not be affected, but merely the tumour cells.

Examples of such neoepitopes are epitopes which are formed by the glycosylation of an EpCAM protein or a Her-2/neu receptor with Lewis Y carbohydrate or appropriately sialylated glycoproteins. When antibodies with specificity for these neoepitopes are produced and prepared, they preferably do not bind to the deglycosylated proteins nor do they bind to the carbohydrate motif on structurally different proteins. It is precisely these antibodies which preferably are suggested as monoclonal antibodies for the passive immunotherapy so as to avoid unspecific interactions and side effects. The identification of the neoepitopes can also be the basis for the development of vaccination antigens, by presenting an immunogen with exactly this epitope. This epitope or a mimic of the epitope can be produced easily from appropriate peptide libraries or by anti-idiotypic antibody techniques or also as a derivative, e.g. a fragment, of a naturally occurring antigen. On the basis of the selected neoepitope, a preparation of an antigen is obtainable which has exactly this neoepitope or the mimic thereof, e.g. an anti-idiotypic antibody, mimotope. Such antigen preparations are valuable active substances for the active immunization of cancer patients or they can also be employed as a diagnostic preparation.

The immunogenic structure according to the invention may be a T-cell helper peptide ligand derived from toxoids like for example tetanus toxoid, diphtheria toxoid or keyhole limpet hemocyanin. The ligands can be of different length, for example of 5 to 50 amino acids length, alternatively of 5 to 30 amino acids or 5 to 20 amino acids.

The use of immunogenic peptides linked to the immunogenic structure can rise immunogenicity when injected to the individual. By way of example, the amino acid sequence may be FKLQTMVKLFNRIKNNVA (SEQ ID No. 1).

The present invention also covers a composition comprising one or more of the immunogenic structures according for the preparation of a medicament for the prophylactic or therapeutic treatment of cancer. The treatment could be by active or passive immunotherapy as discussed further below. Furthermore, the use of an immunogenic structure as disclosed by the invention for the isolation of antibodies suitable for the detection and isolation of tumour cells could also be performed.

By the term antibody, derivative or fragment thereof antibodies of all types are to be understood, in particular monospecific or polyspecific monoclonal antibodies, or also chemically, biochemically or molecular-biologically prepared antibodies, or polyclonal antibodies having a certain specificity, e.g. an immune serum or a fraction of an immune serum.

An antibody utilized according to the invention preferably is a native, i.e. functionally active, antibody. This antibody preferably does not have an attached label or other detection agent so as not to impair its functionality. Native antibodies have the properties of the antibodies naturally occurring in patients. Native antibodies are heterotetrameric glycoproteins composed of two identical light chains and two identical heavy chains.

Yet also an antibody derivative may be used which preferably is selected from the group of antibody fragments, conjugates, homologues or derivatives, or also complexes with additional effector functions. In any event, it is preferred that the antibody derivative contains at least parts of the Fab fragment, preferably together with at least parts of the F(ab')2 fragment, and/or parts of the hinge region and/or the Fc portion of a lambda or kappa antibody.

Furthermore, also a single-chain antibody derivative, such as a so-called single-chain antibody, can be employed according to the invention. An antibody used according to the invention preferably is of the type of an immunoglobulin, such as an IgG, IgE, IgM, IgA or IgD.

By the term nanoparticles clusters of metal or semiconductor atoms are covered which are suitable as substrates for immobilizing a ligand or a plurality of ligands, the ligands comprising carbohydrate groups.

Suitable nanoparticles are for example described in WO 02/32404 and by Crespo R. et al. (Physical Review Letters, 2004, 93, 8, pp 87204-1-4), and are discussed further below.

Where gold clusters are used, normally between 50 and 500 gold atoms may be used to provide core diameters in the nanometer range. For example, the core diameters can be between 50 and 500 nm, between 50 and 250 nm, between 50 and 150 nm.

The ligands are attached covalently to the core of particles. Protocols carrying out this procedure are already well known in the art, covalent binding can for example occur via thiol groups.

Carbohydrate ligands can also be coupled to antibodies. In order to get antibodies that have a plurality of ligands coupled, branched linkers can be used which contain reactive groups in high density. These linkers can bind a plurality of carbohydrate ligands which can then be localized as clustered structures on the antibody.

The immunogenic structures according to the invention can be for the preparation of a medicament for the prophylaxis and treatment of diseases like cancer. This pharmaceutical preparation can be used for immunotherapy.

In a further aspect, the present invention relates to nanoparticles having a core including metal and/or semiconductor atoms, the core being linked to antigenic ligands. The ligands are typically carbohydrate or peptide antigens. The nanoparticles can be used to deliver the antigens and have applications in a wide range of applications, in particular as vaccines in therapeutic applications. In preferred embodiments, the nanoparticles are also linked to adjuvants, for example T-helper stimulatory peptides or carbohydrates which stimulate the innate immune network.

This delivery system has several advantages over prior art methods. The nanoparticle itself may improve the immune response to the antigen by preventing breakdown or clearance of the antigen and by providing the antigen in particulate form.

Where additional adjuvants are used, the invention permits a single delivery vehicle to be used to deliver both antigen and adjuvants, or multiple antigens or adjuvants.

The nanoparticles are of small size, small enough to be taken up by cells to allow the antigen to be presented on the cell surface. Where a T-helper peptide is also conjugated to the nanoparticle, the T-helper peptide may also be presented.

Accordingly, in a further aspect, the present invention provides a nanoparticle which comprises a core including metal and/or semiconductor atoms, wherein the core is covalently linked to a plurality of ligands and the ligands comprise an antigenic ligand. In a preferred embodiment, the ligands also comprise an adjuvant.

The antigen may be, for example, peptide or carbohydrate. In a preferred embodiment, the antigen is a tumour-specific antigen. Preferred carbohydrate tumour antigens include sialyl Tn (STn), sialyl Lewis$^a$ (Le$^a$), sialyl Lewis$^x$ (Le$^x$) or sialyl Lewis$^y$ (Le$^y$) and unssialylated forms thereof. In another preferred embodiment the antigen is a pathogen-specific antigen, such as an antigen of a bacterium, a virus or a parasite. For example, the HIV antigen Man alpha 1-2 Man or the parasite antigen Gal alpha 1-3 Gal may be used.

The adjuvant may stimulate cells of the innate immune response and/or cells of the adaptive immune reponse, such as T cells, in particular T-helper cells. The adjuvant may be a carbohydrate moiety, or a peptide moiety. Preferred carbohydrate moieties include glucose, mannose, fucose and/or N-acetylglucosamine. Preferred peptide moieties include peptides which activate T-helper cells, such as immungenic peptides from bacterial toxins. A particularly preferred peptide moiety comprises the amino acid sequence FKLQTMVKLFNRIKNNVA (SEQ ID No. 1).

Preferably, the nanoparticles of the invention are water soluble. In preferred embodiments, the nanoparticles of the invention have a core with a mean diameter between 0.5 and 10 nm, more preferably between 1 and 2.5 nm. Preferably, the nanoparticles including their ligands has a mean diameter between 10 and 30 nm.

In addition to the antigen and adjuvant, the nanoparticles may comprise one or more further types of ligands. For example, the additional ligands, or groups or domains of ligands, may include one or more peptide, a protein domain, a nucleic acid molecule, a lipidic group, a carbohydrate group, any organic or anionic or cationic group. The carbohydrate group may be a polysaccharide, an oligosaccharide or a monosaccharide group. Preferred ligands include glycoconjugates, thereby forming glyconanoparticles. Where a nucleic acid molecule is present, the nucleic acid molecule may comprise single or double stranded DNA or RNA. In a particularly preferred embodiment, the nanoparticles comprise a membrane translocation signal to aid them in permeating through a cell membrane.

The particles may have more than one species of ligand immobilised thereon, e.g. 2, 3, 4, 5, 10, 20 or 100 different ligands. Alternatively or additionally, a plurality of different types of nanoparticles may be employed together. In preferred embodiments, the mean number of total ligands linked to an individual metallic core of the particle is at least one ligand, more preferably 50 ligands, and most preferably 60 ligands.

The nanoparticle may also comprise a label, such as a fluorescent group, a radionuclide, a magnetic label, a dye, a NMR active atom, or an atom which is capable of detection using surface plasmon resonance. Preferred magnetic labels include paramagnetic groups comprising $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ or lanthanides$^{+3}$. Preferred NMR active atoms include $Mn^{+2}$, $Gd^{+3}$, $EU^{+2}$, $Cu^{+2}$, $V^{+2}$, $Co^{+2}$, $Ni^{+2}$, $Fe^{+2}$, $Fe^{+3}$ or lanthanides$^{+3}$.

The core of the nanoparticle may be a metallic core. Preferably, the metallic core comprises Au, Ag or Cu, for example an alloy selected from Au/Ag, Au/Cu, Au/Ag/Cu, Au/Pt, Au/Pd, Au/Ag/Cu/Pd, Au/Fe, Au/Cu, Au/Gd, Au/Fe/Cu, Au/Fe/Gd or Au/Fe/Cu/Gd.

In some embodiments, the core of the nanoparticle is magnetic. A preferred magnetic nanoparticle core may comprise passive metal atoms and magnetic metal atoms in the core in a ratio between about 5:0.1 and about 2:5. The passive metal may be, for example, gold, platinum, silver or copper, and the magnetic metal is iron or cobalt.

In another aspect, the present invention provides compositions comprising populations of one or more nanoparticles as described herein. In some embodiments, the populations of nanoparticles may have different densities of the same or different ligands attached to the core. In some cases, it may be desirable to encapsulate the nanoparticles to enable the delivery of a plurality of nanoparticles to a target site. Suitable encapsulation technologies are well known to those skilled in the art. The encapsulated population of nanoparticles may be of one, two, three or a plurality of different types. In a preferred embodiment, the composition comprises the nanoparticles and a pharmaceutically acceptable carrier.

In a further aspect, the present invention provides a method of producing a nanoparticle as described herein. Conveniently, the method comprises conjugating the ligands with the core of the nanoparticle by derivatising the ligand a linker and including the derivatised ligand in a reaction mixture from which the core of the nanoparticle is synthesised. During self-assembly of the nanoparticles, the nanoparticle cores attach to the ligand via the linker. The linker may comprise a thiol group, an alkyl group, a glycol group or a peptide group. An exemplary linker group is represented by the general formula HO—$(CH_2)_n$—S—S—$(CH_2)_m$—OH wherein n and m are independently between 1 and 5. When the nanoparticles are synthesized, the —S—S— of the linker splits to form two thio linkers that can each covalently attach to the core of the nanoparticle via a —S— group. In preferred embodiments, the linker group comprises C2, C3, C4, C5, C6, C7, C8, C9, C10, C11, C12, C13 or C15 alkyl and/or C2, C3, C4, C5, C6, C7, C8, C9, C10, C11, C12, C13 or C15 glycol. The linker may be a mixed linker, for example hexaethylene glycol-C11 alkyl.

Different linkers may control whether the peptide is released or remains attached to the nanoparticle. For example, in the case of the BMIX and BC11 peptides described herein, the first two residues of the peptides are FK, which is a cathepsin cleavage site. If this is sufficiently distant from the nanoparticle (using a spacer) the T-helper peptide LQTMVKLFNRIKNNVA (SEQ ID NO: 2) can be released for intracellular processing.

In one embodiment, nanoparticles having cores comprising gold atoms may be synthesised using the protocol first described in WO 02/32404 in which disulphide linkers are employed to derivatise the ligands and the derivatised ligands are reacted with $HAuCl_4$ (tetrachloroauric acid) in the presence of reducing agent to produce the nanoparticles. On this method, the disulphide protected ligand in methanol or water may be added to an aqueous solution of tetrachloroauric acid. A preferred reducing agent is sodium borohydride. These and other features of the method are described WO 02/32404.

In a further aspect, the present invention also provides nanoparticles as described herein for use in preventive or palliative therapy. In particular, the nanoparticles may be for use as a vaccine.

In one aspect, the present invention provides the use of the above defined nanoparticles for the preparation of a medicament for the treatment of a condition ameliorated by the administration of the nanoparticles. For example, the nanoparticles described herein or their derivatives can be formulated in pharmaceutical compositions, and administered to patients in a variety of forms, in particular to treat conditions ameliorated by the administration of an antigen.

In one embodiment, the invention provides the use of nanoparticles of the invention in the preparation of a medicament for the treatment of cancer. The cancer may be, for example, cancer of the colon, pancreas, gut, lung, liner, ovary or bladder.

Also provided is the use of nanoparticles of the invention in the preparation of a medicament for the treatment of infectious disease. The pathogen causing the disease may be viral, bacterial or parasitic.

Examples of specific uses that may be treated according to the present invention are described below, along with other applications of the nanoparticles, both in vitro and in vivo uses.

Embodiments of the present invention will now be described by way of example and not limitation with reference to the accompanying figures.

BRIEF DESCRIPTION OF THE FIGURES

FIG. 4A shows the NMR spectra of the starting mixture (upper) and resulting nanoparticles (lower) for the BC11 I nanoparticle.

FIG. 4B shows the NMR spectra of the starting mixture (upper) and resulting nanoparticles (lower) for the BC11 II nanoparticle.

DETAILED DESCRIPTION

Nanoparticles

Figure 1A:
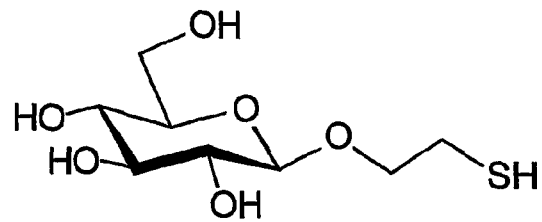
FIG. 1 shows the structure of the ligands Glc (A), Stn (B) and Le$^y$(C).

Nanoparticles are small particles, e.g. clusters of metal or semiconductor atoms, that can be used as a substrate for immobilising ligands.

The nanoparticles of the invention are soluble in most organic solvents and especially water. This can be used in their purification and importantly means that they can be used in solution for presenting the ligand immobilised on the surface of the particle. The fact that the nanoparticles are soluble has the advantage of presenting the ligands in a natural conformation. For therapeutic applications, the nanoparticles are non toxic, soluble and stable under physiological conditions.

Preferably, the nanoparticles have cores having mean diameters between 0.5 and 50 nm, more preferably between 0.5 and 10 nm, more preferably between 0.5 and 5 nm, more preferably between 0.5 and 3 nm and still more preferably between 0.5 and 2.5 nm. When the ligands are considered in addition to the cores, preferably the overall mean diameter of the particles is between 5.0 and 100 nm, more preferably between 5 and 50 nm and most preferably between 10 and 30 nm. The mean diameter can be measured using techniques well known in the art such as transmission electron microscopy.

The core material can be a metal or semiconductor and may be formed of more than one type of atom. Preferably, the core material is a metal selected from Au, Fe or Cu. Nanoparticle cores may also be formed from alloys including Au/Fe, Au/Cu, Au/Gd, Au/Fe/Cu, Au/Fe/Gd and Au/Fe/Cu/Gd, and may be used in the present invention. Preferred core materials are Au and Fe, with the most preferred material being Au. The cores of the nanoparticles preferably comprise between about 100 and 500 atoms (e.g. gold atoms) to provide core diameters in the nanometer range. Other particularly useful core materials are doped with one or more atoms that are NMR active, allowing the nanoparticles to be detected using NMR, both in vitro and in vivo. Examples of NMR active atoms include $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ and lanthanides$^{+3}$, or the quantum dots described elsewhere in this application.

Nanoparticle cores comprising semiconductor atoms can be detected as nanometer scale semiconductor crystals are capable of acting as quantum dots, that is they can absorb light thereby exciting electrons in the materials to higher energy levels, subsequently releasing photons of light at frequencies characteristic of the material. An example of a semiconductor core material is cadmium selenide, cadmium sulphide, cadmium tellurium. Also included are the zinc compounds such as zinc sulphide.

In some embodiments, the core of the nanoparticles may be magnetic and comprise magnetic metal atoms, optionally in combination with passive metal atoms. By way of example, the passive metal may be gold, platinum, silver or copper, and the magnetic metal may be iron or gadolinium. In preferred embodiments, the passive metal is gold and the magnetic metal is iron. In this case, conveniently the ratio of passive metal atoms to magnetic metal atoms in the core is between about 5:0.1 and 2:5. More preferably, the ratio is between about 5:0.1 and about 5:1. As used herein, the term "passive metals" refers to metals which do not show magnetic properties and are chemically stable to oxidation. The passive metals may be diamagnetic or superparamagnetic. Preferably, such nanoparticles are superparamagnetic.

Examples of nanoparticles which have cores comprising a paramagnetic metal, include those comprising $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ and lanthanides$^{+3}$.

Other magnetic nanoparticles may be formed from materials such as MnFe (spinel ferrite) or CoFe (cobalt ferrite) can be formed into nanoparticles (magnetic fluid, with or without the addition of a further core material as defined above. Examples of the self-assembly attachment chemistry for producing such nanoparticles is given in Biotechnol. Prog., 19:1095-100 (2003), J. Am. Chem. Soc. 125:9828-33 (2003), J. Colloid Interface Sci. 255:293-8 (2002).

In some embodiments, the nanoparticle of the present invention or its ligand comprises a detectable label. The label may be an element of the core of the nanoparticle or the ligand. The label may be detectable because of an intrinsic property of that element of the nanoparticle or by being linked, conjugated or associated with a further moiety that is detectable. Preferred examples of labels include a label which is a fluorescent group, a radionuclide, a magnetic label or a dye. Fluorescent groups include fluorescein, rhodamine or tetramethyl rhodamine, Texas-Red, Cy3, Cy5, etc., and may be detected by excitation of the fluorescent label and detection of the emitted light using Raman scattering spectroscopy (Y. C. Cao, R. Jin, C. A. Mirkin, Science 2002, 297: 1536-1539).

In some embodiments, the nanoparticles may comprise a radionuclide for use in detecting the nanoparticle using the radioactivity emitted by the radionuclide, e.g. by using PET, SPECT, or for therapy, i.e. for killing target cells. Examples of radionuclides commonly used in the art that could be readily adapted for use in the present invention include $^{99m}$Tc, which exists in a variety of oxidation states although the most stable is $TcO^{4-}$; $^{32}$P or $^{33}$P; $^{57}$Co; $^{59}$Fe; $^{67}$Cu which is often used as $Cu^{2+}$ salts; $^{67}$Ga which is commonly used a $Ga^{3+}$ salt, e.g. gallium citrate; $^{68}$Ge; $^{82}$Sr; $^{99}$Mo; $^{103}$Pd; $^{111}$In which is generally used as $In^{3+}$ salts; $^{125}$I or $^{131}$I which is generally used as sodium iodide; $^{137}$Cs; $^{153}$Gd; $^{153}$Sm; $^{158}$Au; $^{186}$Re; $^{201}$Tl generally used as a $Tl^+$ salt such as thallium chloride; $^{39}Y^{3+}$; $^{71}Lu^{3+}$; and $^{24}Cr^{2+}$. The general use of radionuclides as labels and tracers is well known in the art and could readily be adapted by the skilled person for use in the aspects of the present invention. The radionuclides may be employed most easily by doping the cores of the nanoparticles or including them as labels present as part of ligands immobilised on the nanoparticles.

Additionally or alternatively, the nanoparticles of the present invention, or the results of their interactions with other species, can be detected using a number of techniques well known in the art using a label associated with the nanoparticle as indicated above or by employing a property of them. These methods of detecting nanoparticles can range from detecting the aggregation that results when the nanoparticles bind to another species, e.g. by simple visual inspection or by using light scattering (transmittance of a solution containing the nanoparticles), to using sophisticated techniques such as transmission electron microscopy (TEM) or atomic force microscopy (AFM) to visualise the nanoparticles. A further method of detecting metal particles is to employ plasmon resonance that is the excitation of electrons at the surface of a metal, usually caused by optical radiation. The phenomenon of surface plasmon resonance (SPR) exists at the interface of a metal (such as Ag or Au) and a dielectric material such as air or water. As changes in SPR occur as analytes bind to the ligand immobilised on the surface of a nanoparticle changing the refractive index of the interface. A further advantage of SPR is that it can be used to monitor real time interactions. As mentioned above, if the nanoparticles include or are doped with atoms which are NMR active, then this technique can be used to detect the particles, both in vitro or in vivo, using techniques well known in the art. Nanoparticles can also be detected using a system based on quantitative signal amplification using the nanoparticle-promoted reduction of silver (I). Fluorescence spectroscopy can be used if the nanoparticles include ligands as fluorescent probes. Also, isotopic labelling of the carbohydrate can be used to facilitate their detection.

The ligands may include an inert carbohydrate component (e.g. glucose) that permits to control at will the density of antigens and carrier in the final construct.

Antigen

An antigen is a molecule that is specifically recognised by cells of the adaptive immune system, i.e. T cells or B cells, or both.

Antigens include protein, carbohydrate, nucleic acid or even small molecules such as toxins. In preferred embodiments of the present invention, the antigen is a tumour-specific antigen, in particular a peptide or carbohydrate tumour-specific antigen. In other preferred embodiments, the antigen is an antigen found on a pathogenic agent, such as a virus, bacterium or parasite.

Examples of carbohydrate tumour-specific antigens include sialylated and unsialylated Lewis structures carried by the carbohydrate chains of glycoproteins and glycolipids on the surface of tumour cells. These antigens are often overexpressed in tumours and appear to be involved in the adhesion of tumour cells to endothelium. For example, sialyl Lewis$^a$ is responsible for adhesion in human colon, pancreas and gastric cancer cells, while sialyl Lewis$^x$ is responsible for the binding of lung, liver and ovarian cancer cells. Sialyl Le$^a$ is overexpressed in colorectal, hepatic and gastric cancers (for review see Ugorski and Laskowska (2002), Acta Biochimican Polonica, 49, 303-311).

Adjuvant

An adjuvant is an agent which enhances the immune response to an antigen. Adjuvants may enhance the antibody response by stimulating cells of the adaptive immune reponse, and/or may act by non-specifically boosting the activity of the innate immune system. In general, antigens which enhance the antibody response do so by either concentrating antigen at appropriate sites where they are more exposed to lymphocytes, or by stimulating the production of cytokines.

When used as a vaccine delivery platform, nanoparticles themselves may act as adjuvants by providing the antigen in particulate form so they are more readily ingested by antigen-presenting cells, such as macrophages. However, this effect can be greatly enhanced by the use of other agents conjugated to the nanoparticles which enhance other aspects of the immune system.

Adjuvants which increase the activity of the innate immune system include carbohydrate moieties such xylose, fucose, mannose and N-acetyl glucosamine. These work in several ways. They may bind secreted molecules that circulate in blood and lymph, which triggers the cleavage of complement components leading to complement fixation. They may also bind surface receptors on phagocytic cells like macrophages, such as CD2-6 (MMR), which stimulate phagocytosis and endocytosis Such adjuvants may also play a role in stimulating the adaptive immune response.

They may bind cell-surface receptors that initiate a signal leading to the release of effector molecules (cytokines). For example, binding of carbohydrate to Toll-like receptors on the surface of dendritic cells causes them to secrete cytokines, including interleukin 6 (IL-6), which interfere with the ability of regulatory T cells to suppress the responses of effector T cells to antigen.

B cells also have Toll-like receptors. When the receptor is bound, it enhances the response of the B cell to the antigen.

Other adjuvants directly stimulate cells of the adaptive immune response. For example, peptides which stimulate helper T lymphocyte (HTL) responses can be used, to amplify CTL response to the antigenic peptide. Such peptides may be, for example, highly immunogenic antigens from tetanus toxoid which produce a non-specific HTL response. The activated HTLs potentiate the proliferation, survivial and effector functions of CTLs.

Such peptides are of particular use in enhancing the immune response to carbohydrate antigens. Though carbohydrate antigens can be bound and internalised by carbohydrate-specific B cells, they cannot activate HTLs which are only activated by peptides. The nanoparticles of the invention can however provoke both B cell and HTL responses as they are conjugated to both the carbohydrate antigen and a HTL-activating peptide. This provides a greatly improved immune response.

Administration and Treatment

The nanoparticle compositions of the invention may be administered to patients by any number of different routes, including enteral or parenteral routes. Parenteral administration includes administration by the following routes: intravenous, cutaneous or subcutaneous, nasal, intramuscular, intraocular, transepithelial, intraperitoneal and topical (including dermal, ocular, rectal, nasal, inhalation and aerosol), and rectal systemic routes.

Administration be performed e.g. by injection, or ballistically using a delivery gun to accelerate their transdermal passage through the outer layer of the epidermis. The nanoparticles can then be taken up, e.g. by dendritic cells, which mature as they migrate through the lymphatic system, resulting in modulation of the immune response and vaccination against the antigen. The nanoparticles may also be delivered in aerosols. This is made possible by the small size of the nanoparticles.

The exceptionally small size of the nanoparticles of the present invention is a great advantage for delivery to cells and tissues, as they can be taken up by cells even when linked to targeting or therapeutic molecules.

The nanoparticles of the invention may be formulated as pharmaceutical compositions that may be in the forms of solid or liquid compositions. Such compositions will generally comprise a carrier of some sort, for example a solid carrier such as gelatine or an adjuvant or an inert diluent, or a liquid carrier such as water, petroleum, animal or vegetable oils, mineral oil or synthetic oil. Physiological saline solution, or glycols such as ethylene glycol, propylene glycol or polyethylene glycol may be included. Such compositions and preparations generally contain at least 0.1 wt % of the compound.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, solutions of the compounds or a derivative thereof, e.g. in physiological saline, a dispersion prepared with glycerol, liquid polyethylene glycol or oils.

In addition to one or more of the compounds, optionally in combination with other active ingredient, the compositions can comprise one or more of a pharmaceutically acceptable excipient, carrier, buffer, stabiliser, isotonicising agent, preservative or anti-oxidant or other materials well known to those skilled in the art. Such materials should be non-toxic and should not interfere with the efficacy of the active ingredient. The precise nature of the carrier or other material may depend on the route of administration, e.g. orally or parenterally.

Liquid pharmaceutical compositions are typically formulated to have a pH between about 3.0 and 9.0, more preferably between about 4.5 and 8.5 and still more preferably between about 5.0 and 8.0. The pH of a composition can be maintained by the use of a buffer such as acetate, citrate, phosphate, succinate, Tris or histidine, typically employed in the range from about 1 mM to 50 mM. The pH of compositions can otherwise be adjusted by using physiologically acceptable acids or bases.

Preservatives are generally included in pharmaceutical compositions to retard microbial growth, extending the shelf life of the compositions and allowing multiple use packaging. Examples of preservatives include phenol, meta-cresol, benzyl alcohol, para-hydroxybenzoic acid and its esters, methyl paraben, propyl paraben, benzalconium chloride and benzethonium chloride. Preservatives are typically employed in the range of about 0.1 to 1.0% (w/v).

Preferably, the pharmaceutically compositions are given to an individual in a prophylactically effective amount or a therapeutically effective amount (as the case may be, although prophylaxis may be considered therapy), this being sufficient to show benefit to the individual. Typically, this will be to cause a therapeutically useful activity providing benefit to the individual. The actual amount of the compounds administered, and rate and time-course of administration, will depend on the nature and severity of the condition being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Handbook of Pharmaceutical Additives, 2nd Edition (eds. M. Ash and I. Ash), 2001 (Synapse Information Resources, Inc., Endicott, N.Y., USA); Remington's Pharmaceutical Sciences, 20th Edition, 2000, pub. Lippincott, Williams & Wilkins; and Handbook of Pharmaceutical Excipients, 2nd edition, 1994. By way of example, and the compositions are preferably administered to patients in dosages of between about 0.01 and 100 mg of active compound per kg of body weight, and more preferably between about 0.5 and 10 mg/kg of body weight.

It will be understood that where treatment of tumours is concerned, treatment includes any measure taken by the physician to alleviate the effect of the tumour on a patient. Thus, although complete remission of the tumour is a desirable goal, effective treatment will also include any measures capable of achieving partial remission of the tumour as well as a slowing down in the rate of growth of a tumour including metastases. Such measures can be effective in prolonging and/or enhancing the quality of life and relieving the symptoms of the disease.

Immunotherapy

The compositions of the invention, such as the immunogenic structures, may be used for the prophylaxis and treatment of diseases like cancer, and more particularly for immunotherapy.

In the present invention, the term "vaccination" means an active immunization, that is an induction of a specific immune response due to administration, e.g. via the subcutaneous, intradermal, intramuscular, oral or nasal routes, of small amounts of an antigen which is recognized by the vaccinated individual as foreign and is therefore immunogenic in a suitable formulation. The antigen is thus used as a "trigger" for the immune system in order to build up a specific immune response against the antigen.

In accordance with the present invention, vaccination may be therapeutic or prophylactic, as is the case with all antimicrobial vaccines. By way of example, it might be possible to achieve a prophylactic protection against the breakout of a cancer disease by vaccination of individuals who do not suffer from cancer. Examples of individuals for whom such a prophylactic vaccination might be applied are individuals who have an increased risk of developing a cancer disease, although this application is not limited to such individuals. Patients being at risk of cancer can already have developed tumours, either as primary tumours or metastases, or show predisposition for cancer.

For the active immunization of cancer patients according to the invention, the immunogenic structures are typically formulated as vaccines. Preferably, such pharmaceutical preparations contain a pharmaceutically acceptable carrier which, by way of example, may further comprise auxiliary substances, buffers, salts and/or preserving agents. The pharmaceutical preparations may, e.g., be used for the prophylaxis and therapy of cancer-associated conditions, such as metastasis formation, in cancer patients. In doing so, antigen-presenting cells are specifically modulated in vivo or also ex vivo so as to generate the immune response against the TAAs.

For the active immunization with the specific antigens or the antigen combination usually a vaccine formulation is used which contains the immunogen—be it a natural TAA or its epitope, mimic or neoepitope mimic, or an immunogenic antibody—mostly at low concentrations, e.g. in an immunogenic amount ranging from 0.01 µg to 10 mg, yet the dosage range can be increased up a range of 100 to 500 mg. Depending on the immunogenicity of the vaccination antigen which is, e.g., determined by sequences of a foreign species or by derivatization, or also depending on the auxiliary substances or adjuvants, respectively, used, the suitable immunogenic dose can be chosen e.g. in the range of from 0.01 µg to 1 mg, preferably 100 µg to 500 µg. A depot vaccine which is to be delivered to the organism over an extended period of time may, however, also contain much higher amounts of vaccination antigen, e.g. at least 1 mg to more than 100 mg.

The concentration will depend on the amount of liquid or suspended vaccine administered. A vaccine usually is provided in ready-to-use syringes or ampoules having a volume ranging from 0.01 to 1 ml, preferably 0.1 to 0.75 ml.

The vaccination antigen of a component of the inventive kit preferably is presented in a pharmaceutically acceptable carrier which is suitable for subcutaneous, intramuscular and also intradermal or transdermal administration. A further mode of administration functions via the mucosal pathway, e.g. vaccination by nasal or peroral administration. If solid substances are employed as auxiliary agent for the vaccine formulation, e.g. an adsorbate, or a suspended mixture, respectively, of the vaccine antigen with the auxiliary agent will be administered. In special embodiments, the vaccine is presented as a solution or a liquid vaccine in an aqueous solvent.

Preferably, vaccination units of a tumor vaccine are already provided in a suitable ready-to-use syringe or ampoule. A stable formulation of the vaccine may advantageously be put on the market in a ready to use form. Although a content of preserving agents, such as thimerosal or other preserving agents with an improved tolerability, is not necessarily required, yet it may be provided in the formulation for a longer stability at storage temperatures of from refrigerating temperatures up to room temperature. The vaccine according to the invention may, however, also be provided in frozen or lyophilized form and may be thawed or reconstituted, respectively, upon demand.

It has proved suitable to increase the immunogenicity of an antibody used according to the invention by employing adjuvants. For this purpose, solid substances or liquid vaccine adjuvants are used, e.g. aluminum hydroxide (Alu-Gel) or aluminum phosphate, growth factors, lymphokines, cytokines, such as IL-2, IL-12, GM-CSF, gamma interferon, or complement factors, such as C3d, further liposome preparations, or also formulations with additional antigens against which the immune system has already generated a strong immune response, such as tetanus toxoid, bacterial toxins, such as Pseudomonas exotoxins, and derivatives of lipid A and lipopolysaccharide.

In case a toxoid peptide is covalently linked to the core structure, the need of adjuvants might be reduced or abolished.

EXAMPLES

Example 1

The preparation and characterization of nanoparticles loaded with carbohydrate antigens, a T-helper carrier and glucose attached to the gold surface is described below.

Figure 1B:
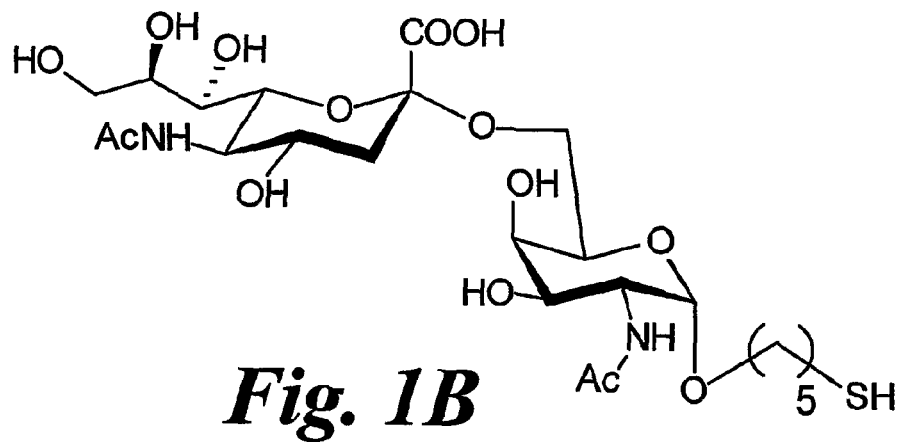
Figure 1C:
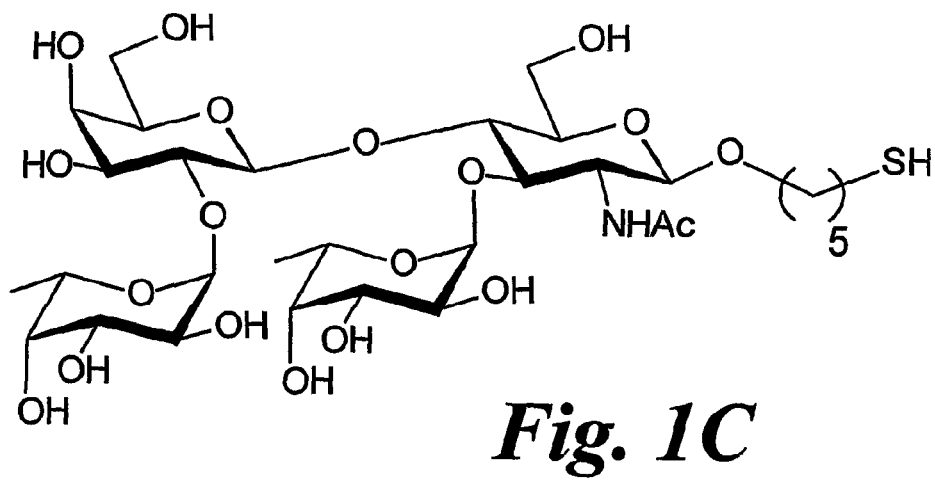

The ligands Glc, STn, and Le$^y$ (FIG. 1) were used. A $C_2$ aliphatic spacer was chosen to attach the glucose residue to the gold surface while a $C_5$ aliphatic linker was used for the attachment of both antigens.

Figure 2:
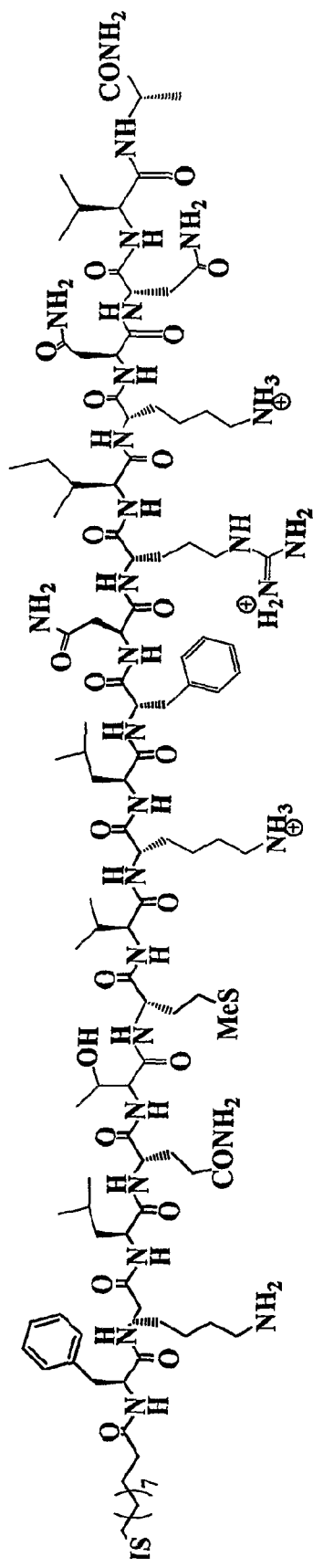
FIG. 2 shows the structure of the T-helper peptide ligand BC11.
Figure 3:
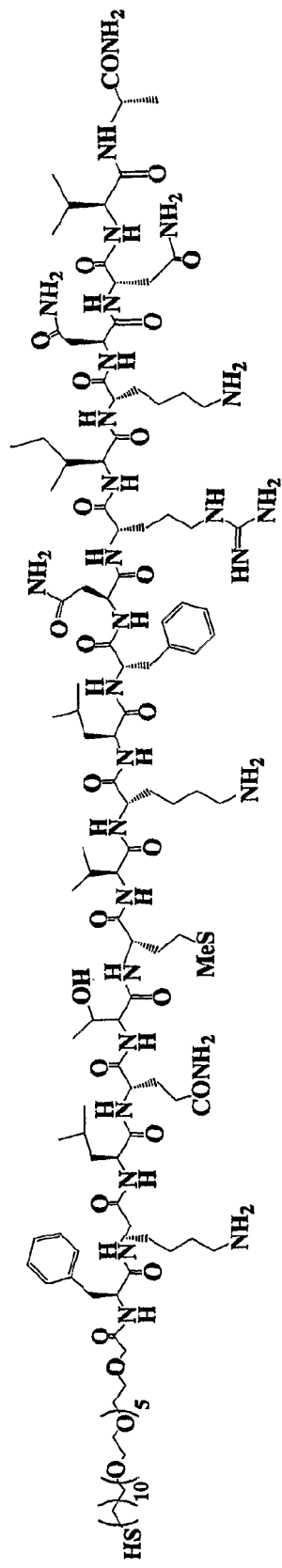
FIG. 3 shows the structure of the T-helper peptide ligand BMIX.
Figure 5A:
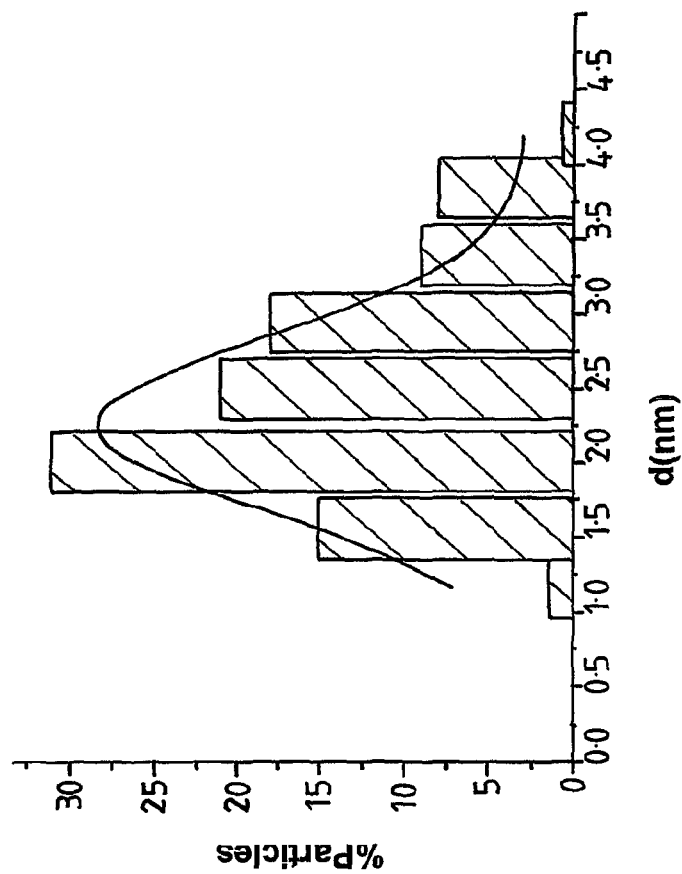
FIG. 5A shows a transmission electron micrograph (left) and size distribution histogram (right) for the BC11 I nanoparticle.
Figure 5A:
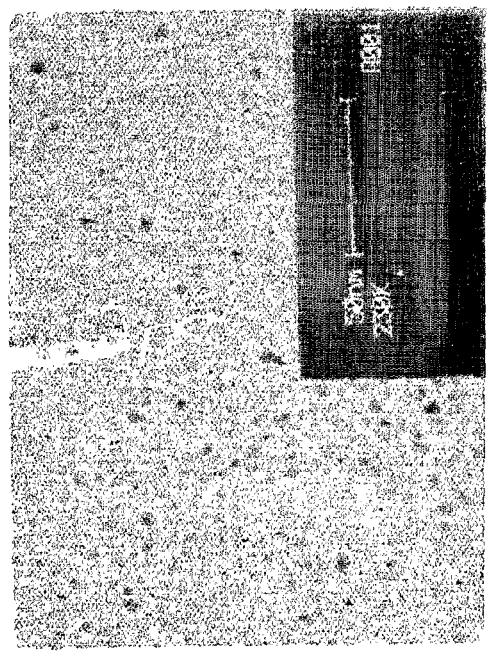
Figure 5B:
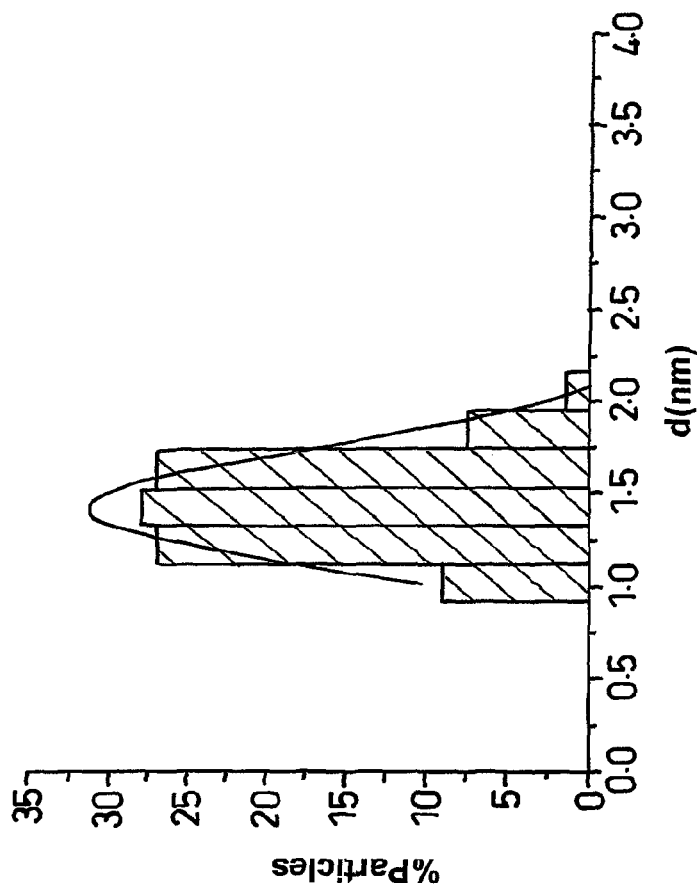
FIG. 5B shows a transmission electron micrograph (left) and size distribution histogram (right) for the BC11 II nanoparticle.
Figure 5B:
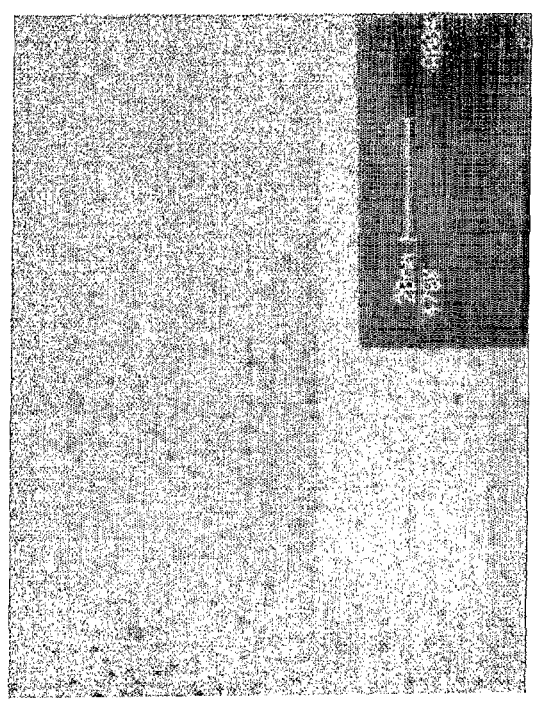
Figure 6:
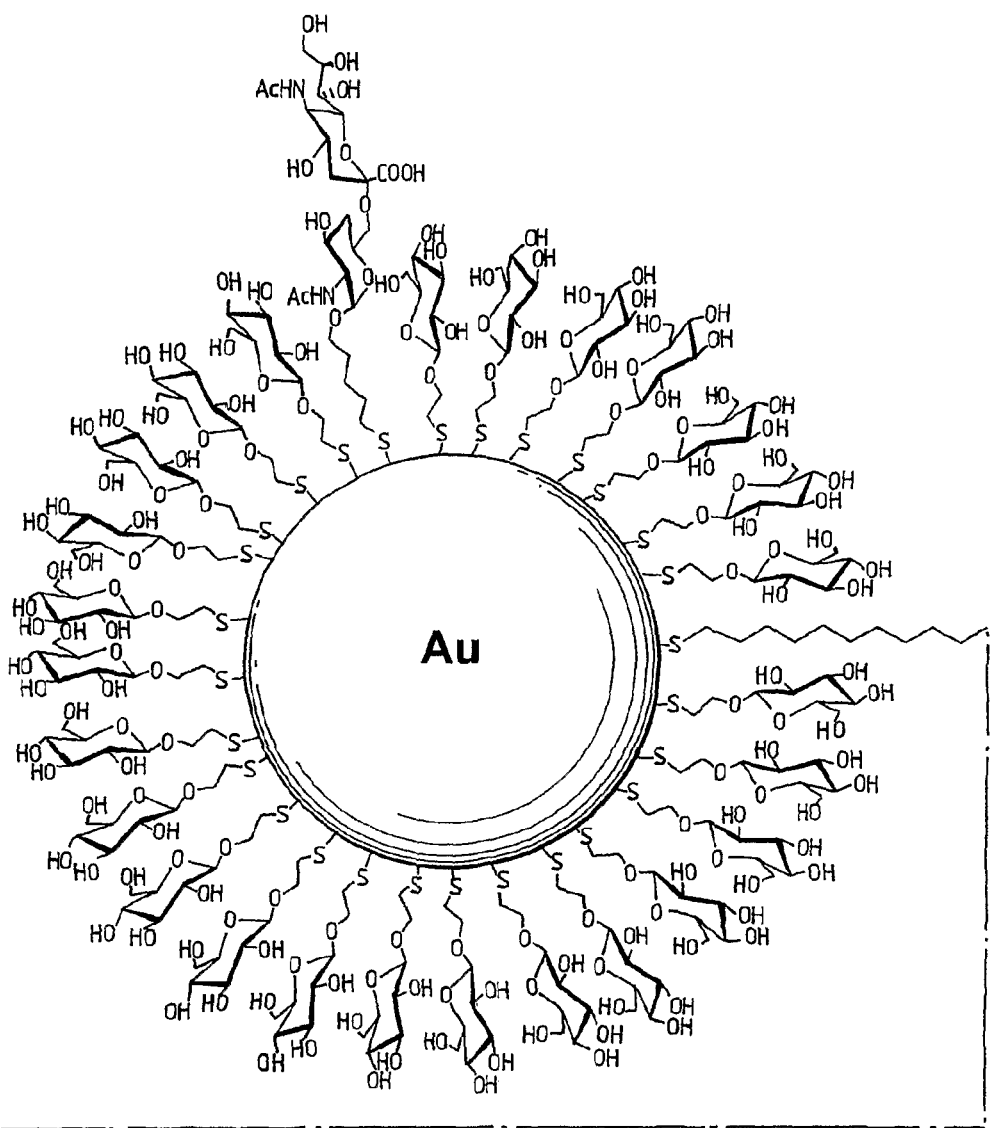
FIG. 6 shows putative schematic representations of the BC11 I nanoparticle.
Figure 6:
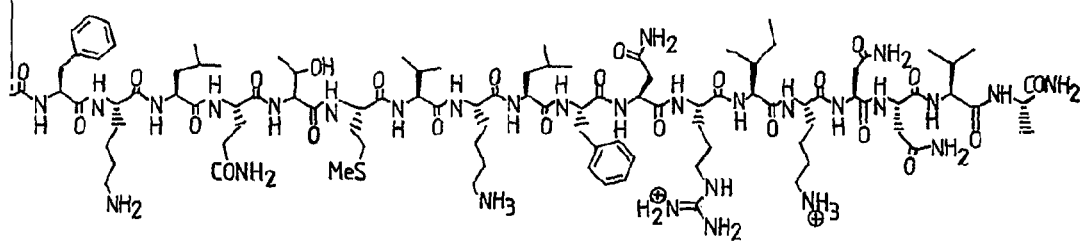

The T-helper peptide ligand BC11 (FIG. 2) was prepared by linking a promiscuous T-cell peptide epitope (FKLQTM-VKLFNRIKNNVA; SEQ ID NO: 1) from tetanus toxoid through the amino terminal group to a $C_{11}$ aliphatic spacer. The T-helper peptide ligand BMIX (FIG. 3) was prepared by linking the same tetanus toxoid T-cell peptide epitope through the amino terminal group to a mixed linker composed of hexaethylene glycol and a $C_{11}$ aliphatic spacer.

For the preparation of the glyconanoparticles, Glc, STn, Le$^y$ and BC11 or BMIX were dissolved in deuterated methanol in the desired proportions and the $^1$H NMR spectra of these solutions were recorded at 500 MHz. The spectra of these mixtures permitted to identify signals unequivocally belonging to the individual components and to confirm that the intensity of these signals corresponded to those expected according to the ratio of the different ligands in the original solution (FIG. 4). After diluting with methanol the mixtures were treated as described below to give the corresponding glyconanoparticles which were repeatedly purified by centrifugal filtering. The $^1$H NMR spectra of these constructs in deuterated water (FIG. 4) indicated that the original ligand ratio was maintained in the obtained GNPs under the used previously established experimental conditions. Also the $^1$H NMR spectra of the supernatants confirmed the proposed ligand ratio.

Following the above procedure, the following glyconanoparticles, were prepared: BC11 I (Glc:STn:BC11 28:1:1), BC11 II (Glc:STn:BC11 20:9:1), BC11 III (Glc:STn:Le$^y$:BC11 18:10:1:1), BC11 IV (Glc:STn:Le$^y$:BC11 18:1:10:1), BMIX I (Glc:STn:BMIX 28:1:1), BMIX II (Glc:STn:BMIX 20:9:1), BMIX III (Glc:STn:Le$^y$:BMIX 18:10:1:1), BMIX IV (Glc:STn:Le$^y$:BMIX 18:1:10:1) BMIX V (Glc:Le$^y$:BMIX 28:1:1) and BMIX VI (Glc:Le$^y$:BMIX 20:9:1).

The mean diameters of these constructs, determined using transmission electron microscopy (TEM) (FIG. 5) were 2.25 nm, 1.45 nm, 2.05 nm and 1.81 nm for BC11 I, BC11 II, BC11 III and BC11 IV respectively and 1.80 nm, 1.55 nm, 2.19 nm, 1.77 nm, 1.64 nm and 1.79 nm for BMIX I, BMIX II, BMIX III, BMIX IV, BMIX V and BMIX VI respectively. From these mean diameters the number of gold atoms in the cluster, chains attached to gold and approximate molecular weight of the GNPs were estimated.[3] These values are given below.

Several further glyconanoparticles (1-4) have been prepared and characterized (data not shown). The composition of these constructs are as follows: 1 (STn, 100%), 2 (Le$^y$ 100%), 3 (Glc:STn:HS(CH$_2$)$_{10}$COOH linker 20:1:1), 4 (Glc:STn:HS(CH$_2$)$_{11}$O(CH$_2$CH$_2$O)$_6$CH$_2$COOH linker 28:1:1).

Experimental Section HAuCl$_4$ and NaBH$_4$ were purchased from Aldrich Chemical Company. For all experiments and solutions, Nanopure water (18.1 mΩ) was used.

Preparation of Peptide BC11-Au-Antigenic Carbohydrates Nanoparticles.

a) BC11 I (Glc:STn:BC11 28:1:1).

Peptide BC11 (3.1 mg, 1.31 μmol) was dissolved in CF$_3$COOD (100 μL) and the solution was concentrated under an argon stream until formation of an oil was observed. Glc (8.8 mg, 36.7 μmol) and STn (0.8 mg, 1.31 μmol) were then added and the mixture was dissolved in CD$_3$OD (500 μL). The $^1$H-NMR spectrum showed a ratio 28:1:1 between the signals of Glc, STn and BC11.

The solution was diluted with MeOH (2.8 mL) and the pH value was adjusted to 1 by addition of trifluoroacetic acid. An aqueous solution of HAuCl$_4$ (286 μL, 0.025M) was added. Then, 1N aqueous solution of NaBH$_4$ (157 μL) was added in several portions with rapid shaking. The black suspension formed was shaken for an additional 2 h and the methanolic layer was separated by decantation[4]. The black solid was dissolved in water (700 μL) and purified by centrifugal filtering (AMICON MW 10000, 30 min, 14000 rpm). The process was repeated twice, until the nanoparticles were free of salts and starting materials. The residue in the AMICON filter was dissolved in 500 μL of water and lyophilised to afford 1.2 mg of BC11 I nanoparticles. TEM: average diameter 2.25 nm, 309 gold atoms, 92 chains, MW=90586.

b) BC11 II (Glc:STn:BC11 20:9:1).

Peptide BC11 (4.0 mg, 1.7 μmol) was dissolved in CF$_3$COOD (100 μL) and the solution was concentrated under an argon stream until the formation of an oil was observed. Glc (8.1 mg, 33.9 μmol) and STn (9.3 mg, 15.2 μmol) were then added and the mixture was dissolved in CD$_3$OD (500 μL). The $^1$H-NMR spectrum showed a ratio 20:9:1 between the signals of Glc, STn and BC11.

The solution was diluted with MeOH (3.7 mL) and the pH value was adjusted to 1 by addition of trifluoroacetic acid. An aqueous solution of HAuCl$_4$ (368 μL, 0.025M) was added. Then, 1N aqueous solution of NaBH$_4$ (202 μL) was added in several portions with rapid shaking. The black suspension formed was shaken for an additional 2 h and the methanolic layer was separated by decantation[4]. The black solid was dissolved in water (500 μL) and purified by centrifugal filtering (AMICON MW 10000, 30 min, 14000 rpm). The process was repeated twice, until the nanoparticles were free of salts and starting materials. The residue in the AMICON filter was dissolved in 500 μL of water and lyophilised to afford 1.8 mg of BC11 II nanoparticles. TEM: average diameter 1.45 nm, 116 gold atoms, 53 chains, MW=45358.

c) BC11 III (Glc:STn:Le$^y$:BC11 18:10:1:1).

Peptide BC11 (2.8 mg, 1.2 μmol) was dissolved in CF$_3$COOD (100 μL) and the solution was concentrated under an argon stream until formation of an oil was observed. Glc (5.1 mg, 21.3 μmol), Le$^y$ (0.9 mg, 1.2 μmol) and STn (7.3 mg, 11.8 μmol) were then added and the mixture was dissolved in CD$_3$OD (500 μL). The $^1$H-NMR spectrum showed a ratio 18:10:1:1 between the signals of Glc, STn, Le$^y$ and BC11.

The solution was diluted with MeOH (2.4 mL) and the pH value was adjusted to 1 by addition of trifluoroacetic acid. An aqueous solution of HAuCl$_4$ (256 μL, 0.025M) was added. Then, 1N aqueous solution of NaBH$_4$ (142 μL) was added in several portions with rapid shaking. The black suspension formed was shaken for an additional 2 h and the methanolic layer was separated by decantation[4]. The black solid was dissolved in water (500 μL) and purified by centrifugal filtering (AMICON MW 10000, 30 min, 14000 rpm). The process was repeated twice, until the nanoparticles were free of salts and starting materials. The residue in the AMICON filter was dissolved in 500 μL of water and lyophilised to afford 0.5 mg of BC11 III nanoparticles. TEM: average diameter 2.05 nm, 225 gold atoms, 71 chains, MW=76661.

d) BC11 IV (Glc:STn:Le$^y$:BC11 18:1:10:1).

Peptide BC11 (2.7 mg, 1.1 μmol) was dissolved in CF$_3$COOD (100 μL) and the solution was concentrated under an argon stream until the formation of an oil was observed. Glc (4.9 mg, 20.6 μmol), Le$^y$ (8.8 mg, 11.4 μmol) and STn (0.7 mg, 1.1 μmol) were then added and the mixture was dissolved in CD$_3$OD (500 μL). The $^1$H-NMR spectrum showed a ratio 18:1:10:1 between the signals of Glc, STn, Le$^y$ and BC11.

The solution was diluted with MeOH (2.3 mL) and the pH value was adjusted to 1 by addition of trifluoroacetic acid. An aqueous solution of HAuCl$_4$ (248 μL, 0.025M) was added. Then, 1N aqueous solution of NaBH$_4$ (137 μL) was added in several portions with rapid shaking. The black suspension formed was shaken for an additional 2 h and the methanolic layer was separated by decantation[4]. The black solid was dissolved in water (500 μL) and purified by centrifugal filtering (AMICON MW 10000, 30 min, 14000 rpm). The process was repeated twice, until the nanoparticles were free of salts and starting materials. The residue in the AMICON filter was dissolved in 500 μL of water and lyophilised to afford 1.2 mg of BC11 IV nanoparticles. TEM: average diameter 1.81 nm, 201 gold atoms, 71 chains, MW=75409.

Preparation of Peptide BMIX-Au-Antigenic Carbohydrates Nanoparticles.

a) BMIX I (Glc:STn:BMIX 28:1:1).

Peptide BMIX (3.5 mg, 1.31 μmol) was dissolved in CF$_3$COOD (100 μL) and the solution was concentrated under an argon stream until formation of an oil was observed. Glc (8.8 mg, 36.6 μmol) and STn (0.8 mg, 1.31 μmol) were then added and the mixture was dissolved in CD$_3$OD (500 μL). The $^1$H-NMR spectrum showed a ratio 28:1:1 between the signals of Glc, STn and BMIX.

The solution was diluted with MeOH (2.7 mL, total volume: 3.2 mL) and the pH value was adjusted to 1 by addition of trifluoroacetic acid. An aqueous solution of HAuCl$_4$ (314 μL, 0.025M) was added. Then, 1N aqueous solution of NaBH$_4$ (157 μL) was added in several portions with rapid shaking. The black suspension formed was shaken for an additional 2 h and the methanolic layer was separated by decantation[2]. The black solid was dissolved in water (700 μL) and purified by centrifugal filtering (AMICON MW 10000, 30 min, 14000 rpm). The process was repeated twice, until the nanoparticles were free of salts and starting materials. The residue in the AMICON filter was dissolved in 500 μL of water and lyophilised to afford 1.0 mg of BMIX I nanoparticles. TEM: average diameter 1.80 nm, 201 gold atoms, 71 chains, MW=63300.

b) BMIX II (Glc:STn:BMIX 20:9:1).

Peptide BMIX (3.5 mg, 1.31 μmol) was dissolved in CF$_3$COOD (100 μL) and the solution was concentrated under an argon stream until the formation of an oil was observed. Glc (6.3 mg, 26.2 μmol) and STn (7.2 mg, 11.7 μmol) were then added and the mixture was dissolved in CD$_3$OD (500 μL). The $^1$H-NMR spectrum showed a ratio 20:9:1 between the signals of Glc, STn and BMIX.

The solution was diluted with MeOH (2.7 mL, total volume: 3.2 mL) and the pH value was adjusted to 1 by addition of trifluoroacetic acid. An aqueous solution of $HAuCl_4$ (314 μL, 0.025M) was added. Then, 1N aqueous solution of $NaBH_4$ (157 μL) was added in several portions with rapid shaking. The black suspension formed was shaken for an additional 2 h. In this, was impossible to separate the methanolic layer by decantation. Then, the volume was reduced to 1 mL, water (700 μL) was added and purified by centrifugal filtering (AMICON MW 10000, 30 min, 14000 rpm). The process was repeated until the nanoparticles were free of salts and starting materials. The residue in the AMICON filter was dissolved in 500 μL of water and lyophilised to afford 2.5 mg of BMIX II nanoparticles. TEM: average diameter 1.55 nm, 140 gold atoms, 53 chains, MW=50567.

c) BMIX III (Glc:STn:Le$^y$:BMIX 18:10:1:1).

Peptide BMIX (3.9 mg, 1.46 μmol) was dissolved in $CF_3COOD$ (100 μL) and the solution was concentrated under an argon stream until the formation of an oil was observed. Glc (6.3 mg, 26.2 μmol), Le$^y$ (1.1 mg, 1.46 μmol) and STn (9.0 mg, 14.6 mmol) were then added and the mixture was dissolved in $CD_3OD$ (500 μL). The $^1$H-NMR spectrum showed a ratio 18:10:1:1 between the signals of Glc, STn, Le$^y$ and BMIX.

The solution was diluted with MeOH (3.2 mL, total volume: 3.7 mL). An aqueous solution of $HAuCl_4$ (350 μL, 0.025M) was added. Then, 1N aqueous solution of $NaBH_4$ (193 μL) was added in several portions with rapid shaking. The black suspension formed was shaken for an additional 2 h and the methanolic layer was separated by decantation[2]. The black solid was dissolved in water (500 μL) and purified by centrifugal filtering (AMICON MW 10000, 30 min, 14000 rpm). The process was repeated twice, until the nanoparticles were free of salts and starting materials. The residue in the AMICON filter was dissolved in 500 μL of water and lyophilised to afford 2.8 mg of BMIX III nanoparticles. TEM: average diameter 2.19 nm, 309 gold atoms, 92 chains, MW=103569.

d) BMIX IV (Glc:STn:Le$^y$:BMIX 18:1:10:1).

Peptide BMIX (3.7 mg, 1.38 μmol) was dissolved in $CF_3COOD$ (100 μL) and the solution was concentrated under an argon stream until the formation of an oil was observed. Glc (6.0 mg, 24.8 μmol), Le$^y$ (10.7 mg, 13.8 μmol) and STn (0.85 mg, 1.38 μmol) were then added and the mixture was dissolved in $CD_3OD$ (500 μL). The $^1$H-NMR spectrum showed a ratio 18:1:10:1 between the signals of Glc, STn, Le$^y$ and BMIX.

The solution was diluted with MeOH (3.0 mL, total volume: 3.5 mL) and the pH value was adjusted to 1 by addition of trifluoroacetic acid. An aqueous solution of $HAuCl_4$ (330 μL, 0.025M) was added. Then, 1N aqueous solution of $NaBH_4$ (182 μL) was added in several portions with rapid shaking. The black suspension formed was shaken for an additional 2 h and the methanolic layer was separated by decantation[2]. The black solid was dissolved in water (500 μL) and purified by centrifugal filtering (AMICON MW 10000, 30 min, 14000 rpm). The process was repeated twice, until the nanoparticles were free of salts and starting materials. The residue in the AMICON filter was dissolved in 500 μL of water and lyophilised to afford 1.8 mg of BMIX IV nanoparticles. TEM: average diameter 1.77 nm, 201 gold atoms, 71 chains, MW=75934.

e) BMIX V (Glc:Le$^y$:BMIX 28:1:1).

Peptide BMIX (3.7 mg, 1.4 μmol) was dissolved in $CF_3COOD$ (100 μL) and the solution was concentrated under an argon stream until formation of an oil was observed. Glc (9.4 mg, 39.1 μmol) and Le$^y$ (1.1 mg, 1.4 μmol) were then added and the mixture was dissolved in $CD_3OD$ (500 μL). The $^1$H-NMR spectrum showed a ratio 28:1:1 between the signals of Glc, Le$^y$ and BMIX.

The solution was diluted with MeOH (3.0 mL, total volume: 3.5 mL) and the pH value was adjusted to 1 by addition of trifluoroacetic acid. An aqueous solution of $HAuCl_4$ (331 mL, 0.025M) was added. Then, 1N aqueous solution of $NaBH_4$ (182 μL) was added in several portions with rapid shaking. The black suspension formed was shaken for an additional 2 h and the methanolic layer was separated by decantation[2]. The black solid was dissolved in water (700 μL) and purified by centrifugal filtering (AMICON MW 10000, 30 min, 14000 rpm). The process was repeated twice, until the nanoparticles were free of salts and starting materials. The residue in the AMICON filter was dissolved in 500 μL of water and lyophilised to afford 0.7 mg of BMIX V nanoparticles. TEM: average diameter 1.64 nm, 140 gold atoms, 53 chains, MW=45568.

f) BMIX VI (Glc:Le$^y$:BMIX 20:9:1).

Peptide BMIX (3.5 mg, 1.31 μmol) was dissolved in $CF_3COOD$ (100 μL) and the solution was concentrated under an argon stream until the formation of an oil was observed. Glc (6.3 mg, 26.2 μmol) and Le$^y$(9.2 mg, 11.8 μmol) were then added and the mixture was dissolved in $CD_3OD$ (500 μL). The $^1$H-NMR spectrum showed a ratio 20:9:1 between the signals of Glc, Le$^y$ and BMIX.

The solution was diluted with MeOH (2.7 mL, total volume: 3.2 mL) and the pH value was adjusted to 1 by addition of trifluoroacetic acid. An aqueous solution of $HAuCl_4$ (314 μL, 0.025M) was added. Then, 1N aqueous solution of $NaBH_4$ (157 μL) was added in several portions with rapid shaking. The black suspension formed was shaken for an additional 2 h. In this, was impossible to separate the methanolic layer by decantation. Then, the volume was reduced to 1 mL, water (700 μL) was added and purified by centrifugal filtering (AMICON MW 10000, 30 min, 14000 rpm). The process was repeated until the nanoparticles were free of salts and starting materials. The residue in the AMICON filter was dissolved in 500 μL of water and lyophilised to afford 1.8 mg of BMIX VI nanoparticles. TEM: average diameter 1.79 nm, 201 gold atoms, 71 chains, MW=73864.

Use of Antigen-Conjugated Nanoparticles to Induce Immune Response

Figure 7:
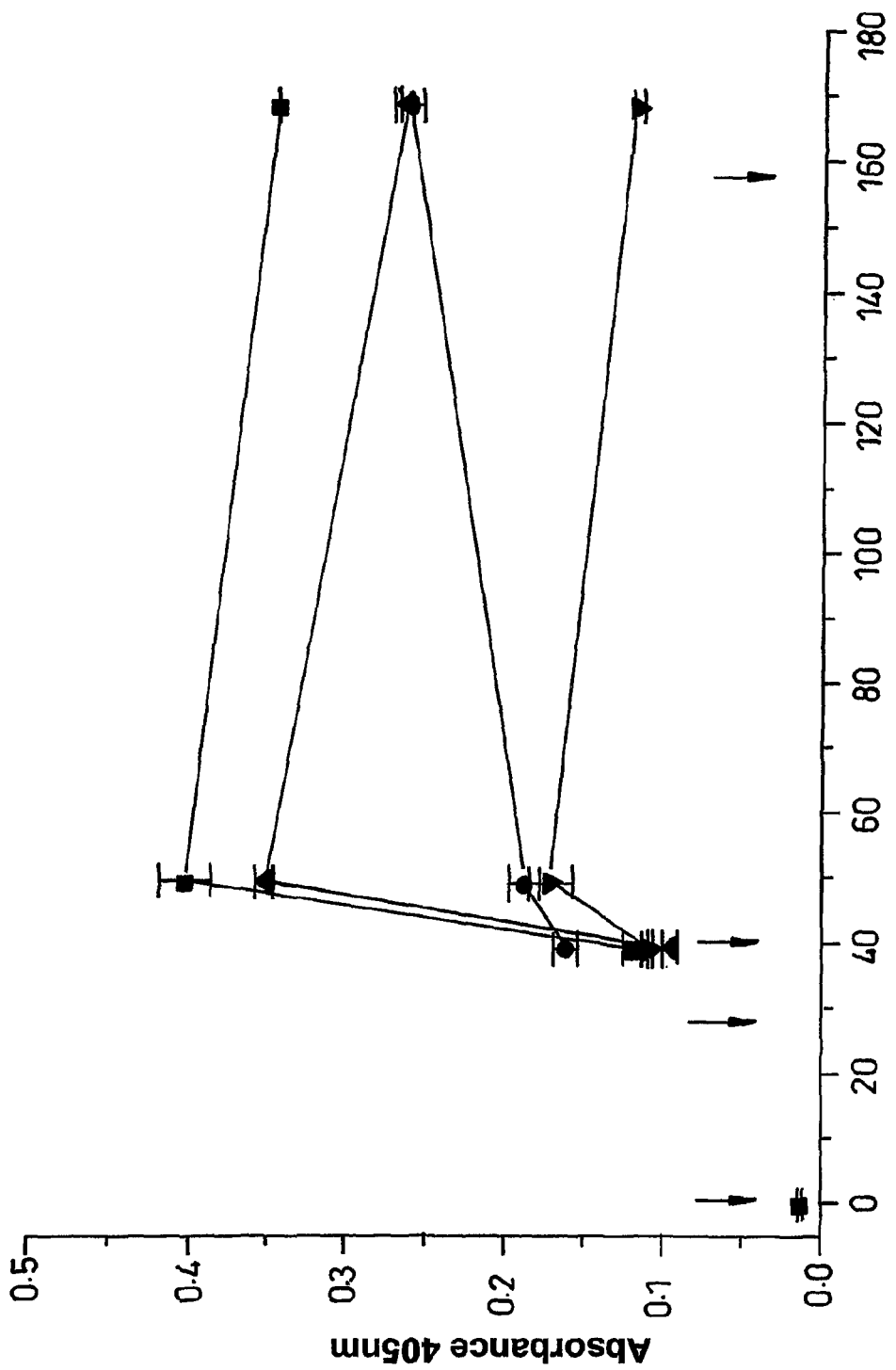
FIG. 7 shows sera titres of IgG against HSA-Le$^y$ from mice inoculated with BC11 I (circles and squares) or BC11 II (triangles). Control serum from non-inoculated mice is shown as a single filled square. Arrows indicate timing of inoculations.
Figure 8:
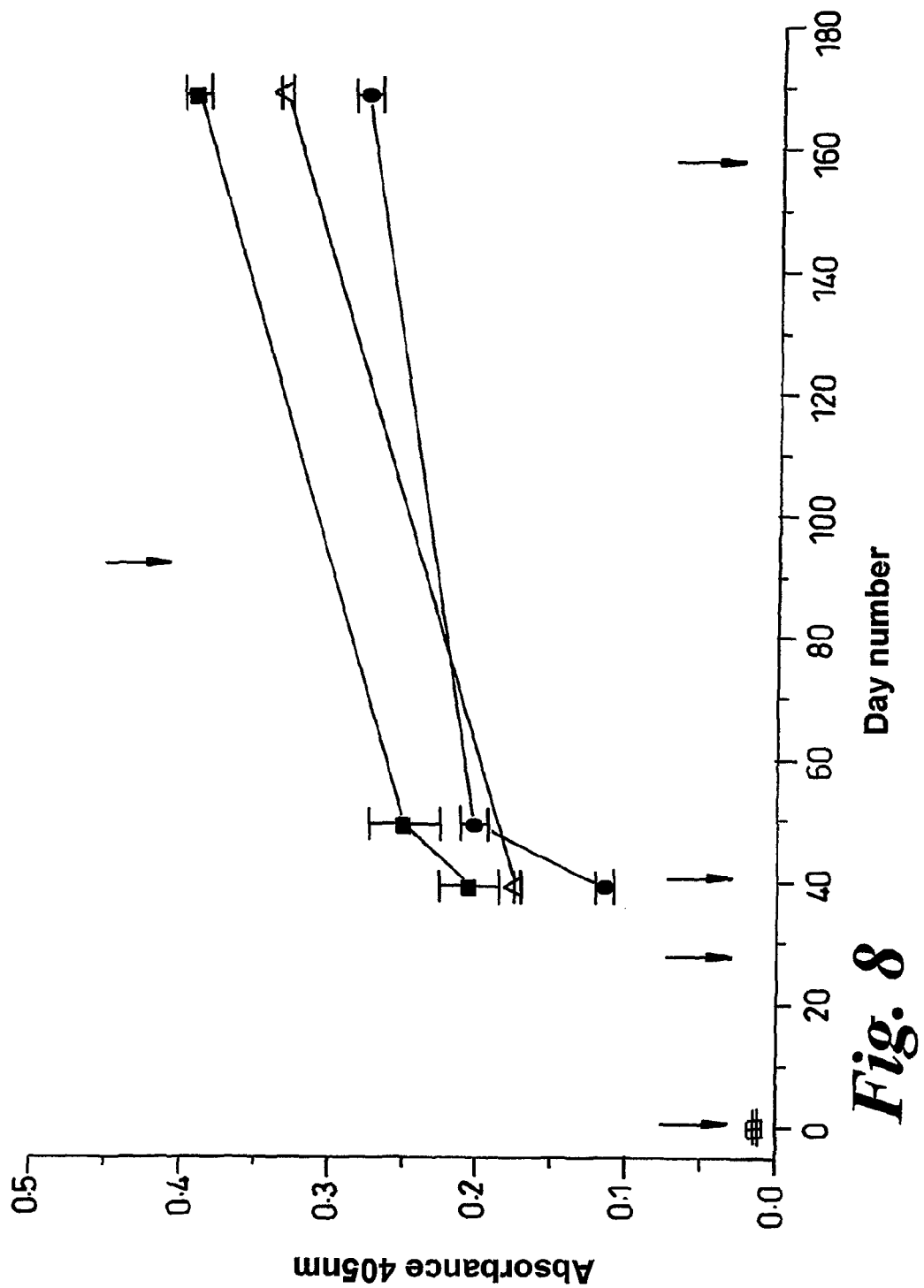
FIG. 8 shows sera titres of IgG against HSA-Le$^y$ from mice inoculated with BC11 III (triangles) or BC11 IV (squares and circles). Control serum from non-inoculated mice is shown as an open square. Arrows indicate timing of inoculations.

Nanoparticles BC11 I, II, III and IV were used to inoculate mice and the immune reaction to the conjugated antigen was monitored. 30 μg nanoparticles were injected in 200 μl adjuvant (Sigma M-6536-MPL+TDM). Four injections of 2×100 μl were given on days 0, 28, 40 and 157. The first three were given subcutaneously and the final injection intraperitoneally. Bleeds were taken on days 39, 48 and 67 and the titre of IgG against HSA-Le$^y$ determined (FIGS. 7 and 8). There is a big difference between the result seen with BC11 I/II and BC11 III/IV. The rise in titer against Le$^y$ in BC11 I/II is a non-specific effect due to the use of the adjuvant. Upon repeat immunization the titers do not increase but start to decrease. In contrast, with BC11 III/IV, the titres increase with booster immunization demonstrating a real immunization effect.

Figure 9:
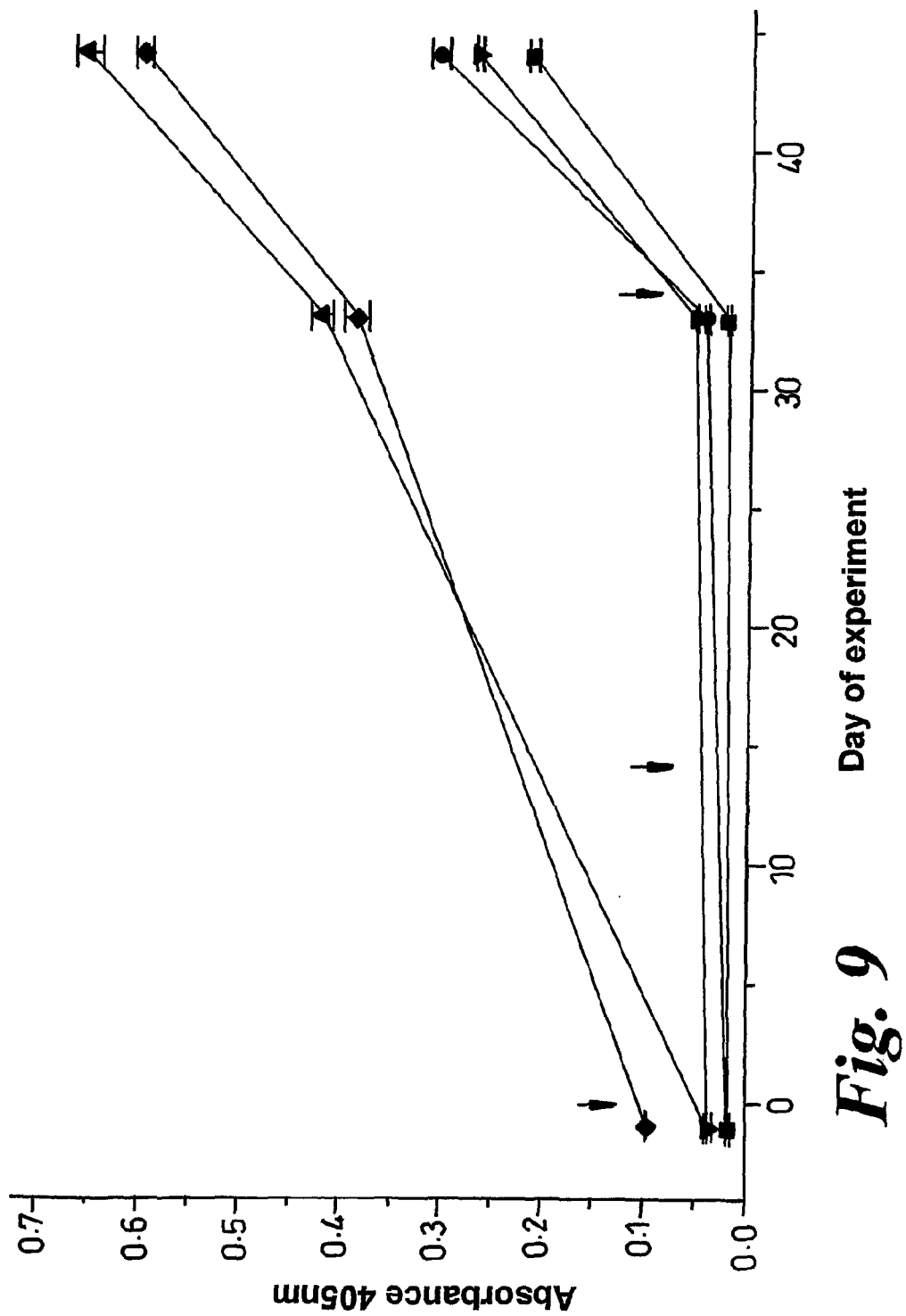
FIG. 9 shows sera titres of IgG against HSA-Le$^y$ from mice inoculated with BC11 II with tetanus toxin priming. Arrows indicate timing of inoculations.

BC11 II was used for inoculation with tetanus toxoid priming. On day 0 animals were injected subcutaneously with 2.35IU of tetanus toxoid from Aventis Pasteur MSD-Diftavax (2 vials made up to a total of 3.4 ml with 0.9% saline and 100 μl administered). On day 14 50 μg nanoparticles in 2×100 μl was injected subcutaneously in adjuvant (Sigma M-6536) and on day 34 50 μg nanoparticles in 2×100 μl was injected intraperitoneally in adjuvant. Bleeds were taken on days 33 and 44. The results for 5 mice are shown in FIG. 9 (different animals are represented by different signals). The first arrow indicates tetanus toxoid priming, the second arrow subcutaneous injection with nanoparticles and the third arrow intraperitoneal injection with nanoparticles.

Example 2

Gold Nanoparticles as Immunogenic Structures

Formulations of gold nanoparticles are made according to the techniques as described in WO 02/32404. Different constructs of gold nanoparticles with a ratio of alpha-Sialyl-Tn: Lewis y=30:3 and 3:30 will be prepared with various densities of the peptide sequence FKLQTMVKLFNRIKNNVA (SEQ ID NO: 1). The rest space can be blocked using Glc-C2. Alternatively, the linker can also be of the sequence FKFQI-LYNSIMG (SEQ ID NO: 3).

The ratio of either Sialyl-Tn or Lewis y or a combination of both linkers can also be increased using the technique according to WO 02/32404. For example, up to several hundreds of carbohydrate groups can easily be linked to the core molecule. The ratios of different ligands can be easily-varied. Alternatively, there can also be one single Sialyl Tn or Lewis y carbohydrate covalently bound to the core molecule.

Antibodies as Immunogenic Structures

Coupling of a SialylTn carbohydrate to HE2 SialylTn-O(CH$_2$)$_3$NH(CH$_2$)$_4$COO-pNp was coupled to HE2. In order to increase the number of SialylTn carbohydrate ligands, branched linkers well known in the art can be used to couple the carbohydrate ligands onto the antibody. The final product was analysed by SEC, LDS-PAGE, Western Blot and different ELISA tests.

Experimental Section
Materials and Methods
HE2 Panorex, 10 mg/ml, Lot170901
  SialylTn-O(CH$_2$)$_3$NH(CH$_2$)$_4$COO-pNp, 2×5 mg, Fa. Lectinity DMF (N,N-Dimethylformamide (anhydrous, Merck)
  Coupling Buffer: 0.1M Na$_2$HPO$_4$+0.15M NaCl (pH=8)
  Formulation Buffer NaCl 0.86%+1 mM Na$_2$HPO$_4$ (pH=6.0)
Procedure
1. 10 mg HE2 (V=10 ml; Conc:10 mg/ml) were dialyzed against 2×700 ml Coupling Buffer using a Slide-A-Lyzer dialysis Cassette at 4° C. for 20 hrs, up to a Volume of 10 ml, concentration according to SEC ~10 mg/ml.
2. 2×5 mg of SialylTn-O(CH$_2$)$_3$NH(CH$_2$)$_4$COO-pNp were dissolved with 2×100 µl DMF (100 µl/Vial).
3. The solution of SialylTn (in DMF) was added to 10 ml (100 mg) ice cold HE2 (in Coupling buffer).
4. Both SialylTn-Vials were rinsed with 100 µl DMF (transfer from Vial 1 to Vial 2), which was also added to the reaction mixture.
5. The reaction mixture was rotated over night (28 hrs) at +4° C. Kinetics of the reaction was observed by SEC (see 5.3.1 and 6.3.1).
6. The final solution of HE2-SialylTn (10 ml, ~10 mg/ml) was dialyzed against 2×800 ml Formulation Buffer using Slide-A-Lyzer dialysis Cassette at 4° C. for 20 hrs.
Analysis
Size Exclusion Chromatography
  Concentrations of HE2-SialylTn were quantified by size exclusion chromatography (SEC) on a ZORBAX GF-250 column in a Dionex system. The HPLC system was tested with gel filtration standard (Fa. BioRAD). HE2 was used as the reference standard for the quantification of HE2-SialylTn. The decrease in the retention time (correlates with increase in molecular weight) correlates with the efficacy of the coupling reaction of SialylTn to HE2. The data received show that the coupling efficacy increases with the reaction time reaching saturation at 23-27 hours.

LDS-PAGE (Lithium Dodecyl Sulphate PAGE)
  LDS-PAGE with Bis-Tris-Gel (4-12%), "SilverXpress™-Stain: see "NuPAGE Bis-Tris-Gel" Instruction Booklet, page 13 Results are shown in FIG. 7.

| lane | Sample | conc. | volume [µl] | preparation |
|---|---|---|---|---|
| 1 | Mark 12 MW Standard | — | 10 | none |
| 2 | HE2 dial. in Coupling buffer | 20 µg/ml | 10 | see SOP |
| 3 | HE2 dial. in Coupling buffer | 10 µg/ml | 10 | see SOP |
| 4 | HE2 dial. in Coupling buffer | 50 µg/ml | 10 | see SOP |
| 5 | HE2 dial. in Coupling buffer | 2.5 µg/ml | 10 | see SOP |
| 6 | HE2SiaTn dial. in Formulation buffer | 20 µg/ml | 10 | see SOP |
| 7 | HE2SiaTn dial. In Formulation buffer | 10 µg/ml | 10 | see SOP |
| 8 | HE2SiaTn dial. in Formulation buffer | 5 µg/ml | 10 | see SOP |
| 9 | HE2SiaTn dial. in Formulation buffer | 2.5 µg/ml | 10 | see SOP |
| 10 | Mark 12 MW Standard | — | 10 | none |

Western Blot
Western Blot with Rabbit×Mouse IgG2a
Procedure:
1. LDS-Gel with Bis-Tris-Gel (4-12%)
2. Western Transfer Instructions see NuPAGE Bis-Tris-Gel Instruction Booklet page 14-20 (with Immobilon transfer membrane PVDF 0.45 µm, Fa. Millipore)
3. Membrane development:
Material:
Conjugate: rabbit×mouse IgG2a-HRP, #61-0220, Fa. Zymed
Staining solution 1: 15 mg HRP-Color Reagent (Fa. Bio-RAD) in 5 ml MetOH.
Staining solution 2: 15 µl 30% H$_2$O$_2$ in 25 ml PBS def. 1×
Procedure:
  Block membrane with 3% Skim Milk Powder in PBS for 1 h at RT.
  Wash membrane with PBS.
  Incubate with conjugate (diluted 1:1000 in PBS) for 1 h at RT.
  Wash membrane with PBS.
  Develop with staining solutions 1+2 and stop with water.
  Western Blot with anti SialylTn CD175s (IgG type)/rat× mouse IgG1-HRP.
Procedure:
1. LDS-PAGE Gel with Bis-Tris-Gel (4-12%).
2. Western Transfer: Instructions see "NuPAGE Bis-Tris-Gel" Instruction Booklet, page 14-20 (using Immobilon transfer membrane PVDF 0.45 µm, Fa. Millipore)
3. Membrane development:
Material:
  Secondary Ab: anti-SialylTn CD175s (IgG type), 90 µg/ml Fa. DAKO, Code. No. M0899, Lot. 089(601).
  Conjugate: rat×mouse IgG1-HRP, Fa. Becton Dickinson, Mat. No. 559626, Batch: 37205.
  3% Skim Milk Powder in PBS deflx.
  Staining solution 1: 15 mg HRP-Color Reagent (Fa. Bio-RAD) in 5 ml MetOH.
  Staining solution 2: 15 µl 30% H$_2$O$_2$ in 25 ml PBS.
Procedure:
  Block membrane with 3% Skim Milk Powder in PBS for 1 h at room temperature (RT).
  Wash membrane with PBS.
  Incubate with Secondary Ab, (concentration 10 µg/ml) V=5 ml, for 1 h at RT.
  Wash membrane with PBS.

Incubate with conjugate (diluted 1:1000 in PBS) for 1 h at RT.

Wash membrane with PBS.

Develop with staining solutions 1+2 and stop with water.

The increase in the molecular weight of the heavy chain of the HE2 antibody after coupling with SialylTn was confirmed by Western Blot and staining with a rabbit anti mouse IgG2a-HRP.

A Standard ELISA was Performed in Order to Show how Much of the Anti-Idiotypic Binding Activity (of HE2) is Retained in the Coupling Product Immobilized IGN111 catches the antiidiotypic HE2 which is detected by anti mouse IgG2a-HRP. It was shown that HE2 is about 2-3 times more reactive than HE2-SialylTn, which indicates that only a very moderate loss of binding occurs after coupling.

A further standard ELISA was performed to detect SialylTn by mouse anti-SialylTn-antibody. Therein the starting material HE2 and the coupling product HE2-SialylTn are immobilized. For detection, anti-SialylTn (mouse IgG)/rat anti mouse IgG1-HRP are used for detection of SialylTn.

The results show that HE2-SialylTn reaction product indeed carries SialylTn in contrast to the HE2 before coupling.

CONCLUSIONS

SialylTn has been successfully coupled to the HE2 antibody. The coupling reaction has a rather prolonged time kinetic reaching saturation approximately after 24 hours. SialylTn has been mainly coupled to the heavy chain of HE2 antibody, whereas the light chain has only been partially coupled with SialylTn. The HE2-SialylTn coupling product retains most of the idiotypic specificity of HE2, and the SialylTn part of this neoglycoprotein is recognized by SialylTn specific antibodies. The endotoxin levels are below detection limit.

REFERENCES

The references mentioned herein are all expressly incorporated by reference in their entirety.

[1] J. M. de la Fuente, A. G. Barrientos, T. C. Rojas, J. Cañada, A. Fernández, S. Penadés, *Angew. Chem. Int. Ed.,* 2001, 40, 2257.

[2] A. G. Barrientos, J. M. de la Fuente, T. C. Rojas, A. Fernández, S. Penadés, *Chem. Eur. J.,* 2003, 9, 1909.

[3] M. J. Hostetler, J. E. Wingate, C. Z. Zhong, J. E. Harris, R. W. Vachet, M. R. Clark, J. D. Londono, S. J. Green, J. J. Stokes, G. D. Wignall, G. L. Clish, M. D. Porter, N. D. Evans, R. W. Murray, *Langmuir,* 1998, 14, 17.

[4] This methanolic layer was concentrated under reduced pressure. The $^1$H-NMR spectrum of the residue showed the same initial ratio, approximately, between Glc, STn, Le$^y$ and BC11 signals.

The invention claimed is:

1. A nanoparticle which comprises:
   a core including metal and/or semiconductor atoms; and
   a plurality of ligands, each of said plurality being covalently linked to the core,
   wherein at least a first ligand of said plurality comprises an antigen which is a pathogen-specific antigen,
   and wherein at least a second ligand of said plurality comprises an adjuvant which is a peptide,
   and wherein at least a third ligand of said plurality is a carbohydrate-containing ligand, the carbohydrate component of which is a monosaccharide and wherein said third ligand blocks core surface space not occupied by said first and second ligands, thereby controlling the density of said first and second ligands.

2. The nanoparticle of claim 1, wherein the adjuvant stimulates the innate immune response.

3. The nanoparticle of claim 1, wherein the adjuvant stimulates a T cell response.

4. The nanoparticle of claim 1, wherein the peptide activates T helper cells.

5. The nanoparticle of claim 4, wherein the peptide comprises a protease cleavage site.

6. The nanoparticle of claim 5, wherein the peptide comprises the amino acid sequence FKLQTMVKLFNRIKNNVA (SEQ ID NO: 1).

7. The nanoparticle of claim 1, wherein the pathogen is a bacterium, a virus or a parasite.

8. The nanoparticle of claim 1, wherein at least one of the plurality of ligands is attached to the nanoparticle core via a thiol linker group.

9. The nanoparticle of claim 1, wherein the core of the nanoparticle comprises a magnetic label.

10. The nanoparticle of claim 9, wherein the magnetic label is a paramagnetic group comprising $Mn^{+2}$, $Gd^{+3}$, $Eu^{+2}$, $cu^{+2}$, $V^{+2}$, $Co^{+2}$, $Ni^{+2}$, $Fe^{+2}$, $Fe^{+3}$ or $lanthanides^{+3}$.

11. The nanoparticle of claim 1, wherein the nanoparticle is water soluble.

12. The nanoparticle of claim 1, wherein the core of the nanoparticle has a mean diameter between 0.5 and 10 nm.

13. The nanoparticle of claim 1, wherein the core of the nanoparticle has a mean diameter between 1 and 2.5 nm.

14. The nanoparticle of claim 1, wherein the nanoparticle including its ligands has a mean diameter between 10 and 30 nm.

15. The nanoparticle of claim 1, wherein the core is a metallic core.

16. The nanoparticle of claim 15, wherein the metallic core comprises Au, Ag or Cu.

17. The nanoparticle of claim 15, wherein the metallic core is an alloy selected from Au/Ag, Au/Cu, Au/Ag/Cu, Au/Pt, Au/Pd, Au/Ag/Cu/Pd, Au/Fe, Au/Cu, Au/Gd, Au/Fe/Cu, Au/Fe/Gd or Au/Fe/Cu/Gd.

18. The nanoparticle of claim 15, wherein the core of the nanoparticle is magnetic.

19. The nanoparticles of claim 18, wherein nanoparticle comprises passive metal atoms and magnetic metal atoms in the core in a ratio between about 5:0.1 and about 2:5.

20. The nanoparticle of claim 19, wherein the passive metal is gold, platinum, silver or copper, and the magnetic metal is iron or cobalt.

21. The nanoparticle of claim 1, wherein the core comprises semiconductor atoms.

22. The nanoparticle of claim 21, wherein the core acts as a quantum dot.

23. A composition comprising a population of more than one of the nanoparticles of claim 1.

24. A composition according to claim 23 further comprising a pharmaceutically acceptable carrier.

25. The nanoparticle of claim 1, wherein said pathogen-specific antigen is selected from the group consisting of: HIV antigen Man alpha 1-2 Man and parasite antigen Gal alpha 1-3 Gal.

26. The nanoparticle of claim 1, wherein said monosaccharide is glucose.

* * * * *

SEQUENCE LISTING

```
<160> NUMBER OF SEQ ID NOS: 3

<210> SEQ ID NO 1
<211> LENGTH: 18
<212> TYPE: PRT
<213> ORGANISM: Artificial sequence
<220> FEATURE:
<223> OTHER INFORMATION: T-cell peptide epitope from tetanus toxoid

<400> SEQUENCE: 1

Phe Lys Leu Gln Thr Met Val Lys Leu Phe Asn Arg Ile Lys Asn Asn
1               5                   10                  15

Val Ala

<210> SEQ ID NO 2
<211> LENGTH: 16
<212> TYPE: PRT
<213> ORGANISM: Artificial sequence
<220> FEATURE:
<223> OTHER INFORMATION: T-helper peptide

<400> SEQUENCE: 2

Leu Gln Thr Met Val Lys Leu Phe Asn Arg Ile Lys Asn Asn Val Ala
1               5                   10                  15

<210> SEQ ID NO 3
<211> LENGTH: 12
<212> TYPE: PRT
<213> ORGANISM: Artificial sequence
<220> FEATURE:
<223> OTHER INFORMATION: Linker

<400> SEQUENCE: 3

Phe Lys Phe Gln Ile Leu Tyr Asn Ser Ile Met Gly
1               5                   10
```